US010925558B2

(12) United States Patent
Kim et al.

(10) Patent No.: US 10,925,558 B2
(45) Date of Patent: Feb. 23, 2021

(54) X-RAY DETECTOR AND METHOD FOR CONTROLLING THE SAME

(71) Applicant: SAMSUNG ELECTRONICS CO., LTD., Suwon-si (KR)

(72) Inventors: Young Ik Kim, Suwon-si (KR); Sung Woo Lee, Suwon-si (KR); Un Cheol Kim, Suwon-si (KR); Jeong Sik Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 15 days.

(21) Appl. No.: 16/206,399

(22) Filed: Nov. 30, 2018

(65) Prior Publication Data
US 2019/0167215 A1 Jun. 6, 2019

(30) Foreign Application Priority Data

Dec. 1, 2017 (KR) .......................... 10-2017-0164296

(51) Int. Cl.
A61B 6/00 (2006.01)
(52) U.S. Cl.
CPC ............... A61B 6/44 (2013.01); A61B 6/00 (2013.01); A61B 6/4283 (2013.01); A61B 6/4405 (2013.01); A61B 6/4411 (2013.01); A61B 6/4452 (2013.01); A61B 6/467 (2013.01); A61B 6/54 (2013.01); A61B 6/56 (2013.01); A61B 6/4007 (2013.01); A61B 6/4233 (2013.01); A61B 6/4266 (2013.01); A61B 6/4494 (2013.01); A61B 6/548 (2013.01)

(58) Field of Classification Search
CPC ............ A61B 6/44; A61B 6/00; A61B 6/4283
See application file for complete search history.

(56) References Cited

U.S. PATENT DOCUMENTS 9,791,910 B1* 10/2017 Brown ................. G06F 1/3206
2009/0012821 A1* 1/2009 Besson ................. G06Q 50/24
705/3
2010/0123083 A1* 5/2010 Petrick ................ A61B 6/4233
250/370.09

(Continued)

FOREIGN PATENT DOCUMENTS

JP 2009-50692 A 3/2009
JP 2011-62425 A 3/2011

(Continued)

OTHER PUBLICATIONS

Communication dated Mar. 15, 2019, issued by the European Patent Office in counterpart European Application No. 18209571.1.

(Continued)

Primary Examiner — Hugh Maupin
(74) Attorney, Agent, or Firm — Sughrue Mion, PLLC

(57) ABSTRACT

The X-ray detector includes a sensor module provided with at least one sensor detecting an event, a communication interface connectable to at least one workstation, and a controller. The controller determines occurrence or non-occurrence of the predefined event based on an output value of the sensor module, and performs a configuration operation of the communication interface based on configuration information corresponding to the generated predefined event when occurrence of the predefined event is determined.

22 Claims, 19 Drawing Sheets

(56) References Cited

U.S. PATENT DOCUMENTS

| | | |
|---|---|---|
| 2014/0295767 A1 | 10/2014 | Iijima |
| 2017/0227660 A1 | 8/2017 | Zhang et al. |
| 2018/0368801 A1* | 12/2018 | Allen .................. A61B 6/4283 |
| 2019/0101495 A1* | 4/2019 | Tognina ................ A61B 90/94 |
| 2019/0327161 A1* | 10/2019 | Cannell .................. H04L 67/18 |

FOREIGN PATENT DOCUMENTS

| | | |
|---|---|---|
| KR | 10-2015-0053708 A | 5/2015 |
| KR | 10-2016-0010222 A | 1/2016 |
| KR | 10-2016-0063074 A | 6/2016 |

OTHER PUBLICATIONS

International Search Report (PCT/ISA/210) dated Mar. 26, 2019 issued by the International Searching Authority in International Application No. PCT/KR2018/015134.

\* cited by examiner

FIG. 5

| SENSOR | AP INFORMATION |
|---|---|
| SENSOR 1 | WAP #1 Configuration Data |
| SENSOR 2 | WAP #2 Configuration Data |
| SENSOR 3 | WAP #3 Configuration Data |
| SENSOR 4 | WAP #4 Configuration Data |

FIG. 7

| SENSOR IN WHICH EVENT HAS OCCURRED | W/S INFORMATION |
|---|---|
| SENSOR 1 | W/S #1 ID |
| SENSOR 2 | W/S #2 ID |
| SENSOR 3 | W/S #3 ID |
| SENSOR 4 | W/S #4 ID |

X-RAY DETECTOR AND METHOD FOR CONTROLLING THE SAME

CROSS-REFERENCE TO RELATED APPLICATION(S)

This application is based on and claims priority under 35 U.S.C. § 119 to Korean Patent Application No. 10-2017-0164296, filed on Dec. 1, 2017, in the Korean Intellectual Property Office, the disclosure of which is incorporated by reference herein in its entirety.

BACKGROUND

1. Field

The disclosure relates to a portable X-ray detector and a method for controlling the same.

2. Description of Related Art

X-ray imaging apparatuses irradiate an object with X-rays and acquire an image of the object using X-rays having passed through the object. X-ray transmittance varies according to properties of materials constituting the object, and thus, an internal structure of the object may be imaged by detecting the intensity of X-rays having passed through the object.

In order to acquire X-ray images using the X-ray imaging apparatus, an X-ray detector detects X-rays having passed through the object being irradiated with the X-rays emitted from the X-ray source.

Recently, portable X-ray detectors that can be carried by the humans have been widely used.

SUMMARY

In accordance with an aspect of the disclosure, there is provided an X-ray detector for allowing a sensor module embedded therein to detect a predefined event, and automatically performing network configuration (i.e., network setting) according to access point (AP) information or workstation information corresponding to the detected event, such that a user of the X-ray detector does not need to manually change configuration information of the X-ray detector one by one even when the X-ray detector is used in a plurality of imaging rooms or in a plurality of X-ray imaging apparatuses, resulting in greater convenience of the user, as well as to provide a method for controlling the same.

In accordance with an aspect of the disclosure, there is provided an X-ray detector apparatus and a method for controlling the same. The X-ray detector apparatus may be used as a plurality of X-ray detectors within only one imaging room. In this case, if any one of the X-ray detectors contained in the X-ray detector apparatus detects a predefined event using an embedded sensor module therein, the corresponding X-ray detector having detected the predefined event may transmit identification (ID) information thereof and a signal indicating occurrence of the event to a workstation, and may be automatically paired with the workstation, such that the user can easily and correctly recognize which one of the plurality of X-ray detectors will be used for X-ray imaging.

Additional aspects of the invention will be set forth in part in the description which follows and, in part, will be obvious from the description, or may be learned by practice of the invention.

In accordance with an aspect of the disclosure, an X-ray detector includes a sensor module provided with at least one sensor detecting an event, a communication interface connectable to at least one workstation, and a controller configured to determine occurrence or non-occurrence of the predefined event based on an output value of the sensor module, and perform a configuration operation of the communication interface based on configuration information corresponding to the generated predefined event when occurrence of the predefined event is determined.

The sensor module may include at least one of a magnetic sensor, an optical sensor, an infrared (IR) sensor, an ultrasonic sensor, an acceleration sensor, a touch sensor, a gyro sensor, and a temperature sensor.

The sensor module may include as many sensors either as the number of the at least one workstation or as the number of APs needed to connect the at least one workstation to the communication interface.

The controller may perform a configuration operation of the communication interface based on workstation information or AP information corresponding to a sensor having detected the predefined event among the at least one sensor contained in the sensor module.

If occurrence of the predefined event is determined, the controller may perform a configuration action of the communication interface based on configuration information corresponding to either category information of the generated event or information about how many times the event has occurred.

The controller may perform a configuration action of the communication interface based on workstation information or AP information corresponding to the number of generated events.

If occurrence of the predefined event is determined, the controller may transmit imaging mode information corresponding to the generated event to the workstation connected to the communication interface.

If occurrence of the predefined event is determined, the controller may configure a drive mode of the X-ray detector according to information about a drive mode corresponding to the generated event.

The X-ray detector may further include a storage configured to match AP information or workstation information corresponding to each of the predefined events to the respective predefined events, and store the matched information.

In accordance with an aspect of the disclosure, an X-ray detector includes a sensor module provided with at least one sensor detecting an event, a communication interface connectable to at least one workstation, and a controller configured to determine occurrence or non-occurrence of the predefined event based on an output value of the sensor module, and transmit an event occurrence signal and ID information of the X-ray detector to a workstation connected to the communication interface when occurrence of the predefined event is determined.

If occurrence of the predefined event is determined, the controller may transmit imaging mode information corresponding to the generated event to the workstation connected to the communication interface.

If occurrence of the predefined event is determined, the controller may configure a drive mode of the X-ray detector according to drive mode information corresponding to the generated event.

The sensor module may include as many sensors as the number of the imaging modes.

The controller may transmit imaging mode information corresponding to a sensor having detected the predefined event among the at least one sensor contained in the sensor module, to a workstation connected to the communication interface.

In accordance with an aspect of the disclosure, a method for controlling an X-ray detector includes matching configuration information of corresponding communication interfaces to the respective predefined events, and storing the matched information, determining occurrence or non-occurrence of the predefined event based on an output value of a sensor module, and if occurrence of the predefined event is determined, performing a configuration operation of the communication interface based on configuration information corresponding to the generated event.

The sensor module may include at least one of a magnetic sensor, an optical sensor, an IR sensor, an ultrasonic sensor, an acceleration sensor, a touch sensor, a gyro sensor, and a temperature sensor.

The sensor module may include as many sensors either as the number of the at least one workstation or as the number of APs needed to connect the at least one workstation to the communication interface.

The performing the configuration operation of the communication interface may include performing a configuration action of the communication interface based on workstation information or AP information corresponding to a sensor having detected the predefined event among the at least one sensor contained in the sensor module.

The method may further include, if the occurrence of the predefined event is determined, performing a configuration action of the communication interface based on configuration information corresponding to either category information of the generated event or information about how many times the event has occurred.

The performing the configuration action of the communication interface may include performing a configuration action of the communication interface based on workstation or AP information corresponding to the number of generated events.

The method may further include, if occurrence of the predefined event is determined, configuring an imaging mode of the X-ray detector according to imaging mode information corresponding to the generated event.

The configuring the imaging mode of the X-ray detector may include, after completion of the configuration action of the communication interface, transmitting imaging mode information corresponding to the generated event to a workstation connected to the communication interface.

The method may further include, if occurrence of the predefined event is determined, configuring a drive mode of the X-ray detector according to drive mode information corresponding to the generated event.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 5 is a conceptual diagram illustrating one example of information stored in a storage of an X-ray detector according to an embodiment.

FIG. 7 is a conceptual diagram illustrating an example of information stored in a storage of an X-ray detector according to an embodiment.

DETAILED DESCRIPTION

Figure 1:
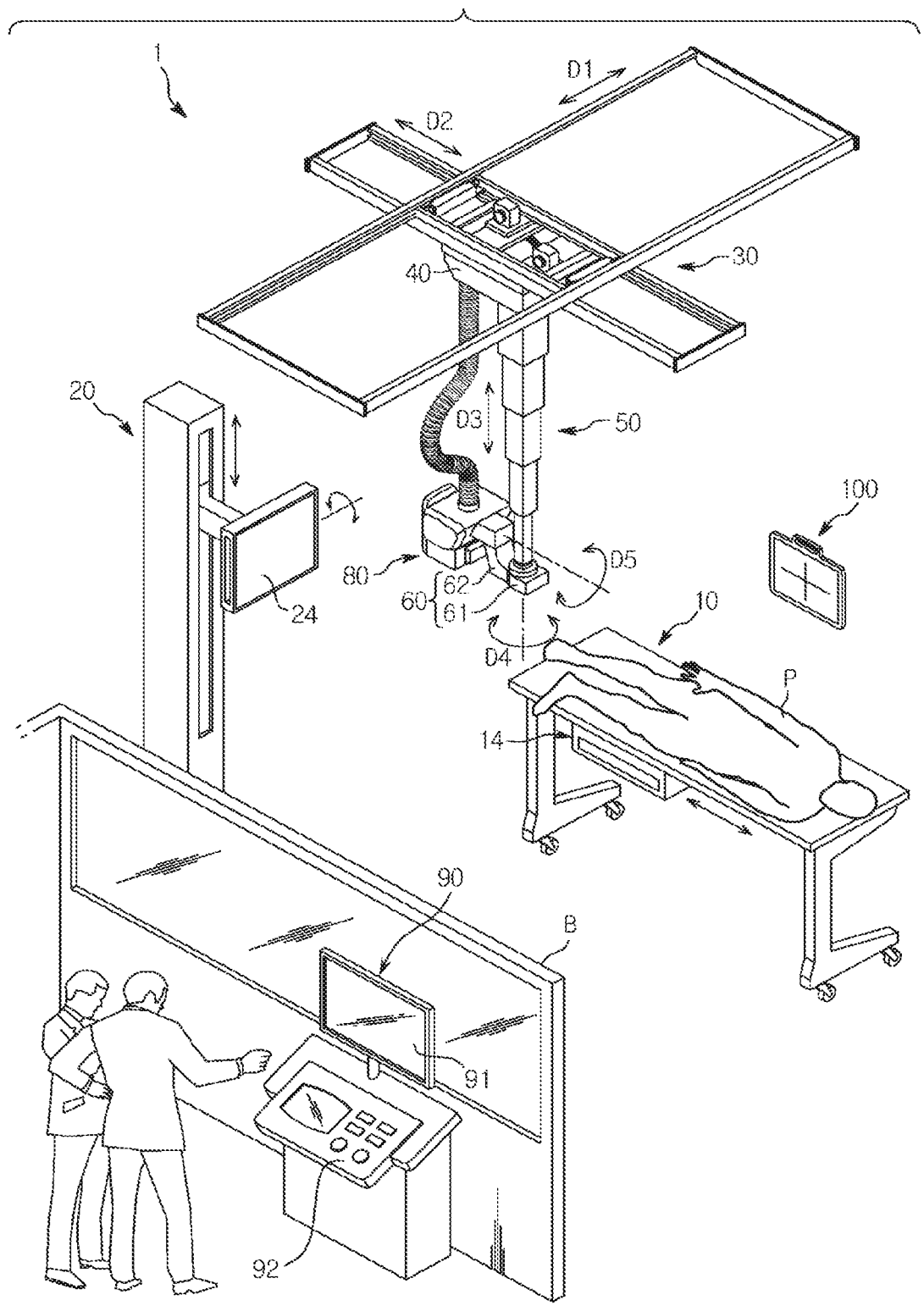
FIG. 1 is a control block diagram illustrating an X-ray imaging apparatus to which an X-ray detector can be applied according to an embodiment.

Reference will now be made in detail to the embodiments of the disclosure, examples of which are illustrated in the accompanying drawings, wherein like reference numerals refer to like elements throughout. It should be noted that the specification does not describe all the constituent elements of the embodiments, and general matters well known to those skilled in the art and redundant matters of the embodiments will not be described herein for clarity.

Throughout the specification, terms " . . . part", " . . . module", " . . . member", " . . . block", and the like mean an element capable of being implemented by hardware, software, or a combination thereof. As used in the specification and appended claims, the term " . . . parts", " . . . modules", " . . . members", or " . . . blocks" may be implemented by a single constituent element, or the term " . . . part", " . . . module", " . . . member", or " . . . block" may include a plurality of constituent elements.

Throughout the specification, if it is assumed that a certain part is connected (or coupled) to another part, the term "connection or coupling" means that the certain part is directly connected (or coupled) to another part and/or is indirectly connected (or coupled) to another part. Here, indirect connection (or indirect coupling) may conceptually include connection (or coupling) over a wireless communication network.

Throughout the specification, if it is assumed that a certain part includes a certain component, the term "comprising or including" means that a corresponding component may further include other components unless context clearly indicates otherwise.

Throughout the specification, if it is described that a certain member is "located ahead of" or "located behind" another element, the terms "located ahead of" or "located behind" mean that the element may be arranged to contact the another element or the intervening elements may be present between two elements.

In description of the disclosure, the terms "first" and "second" may be used to describe various components, but the components are not limited by the terms. These terms may be used to distinguish one component from another component. For example, a first component may be called a second component and a second component may be called a first component without departing from the scope of the disclosure. The term "and/or" may include a combination of a plurality of items or any one of a plurality of items.

The terms "a", "an", "one", "the" and other similar terms include both singular and plural forms, unless context clearly dictates otherwise.

Identification numbers for use in respective operations to be described later are used for convenience of description and better understanding of the disclosure, do not describe the order or sequence of the respective operations of the disclosure, and the respective operations of the disclosure may be carried out in a different way from the order written in the disclosure, unless context of each operation clearly indicates a specific order.

Expressions such as "at least one of" and "at least one among," when preceding a list of elements, modify the entire list of elements and do not modify the individual elements of the list. For example, the expressions "at least one of a, b, and c" and "at least one of a, b, or c" should be understood as including only a, only b, only c, both a and b, both a and c, both b and c, or all of a, b, and c.

FIG. 1 is a control block diagram illustrating an X-ray imaging apparatus 1 to which an X-ray detector can be applied according to an embodiment.

Referring to FIG. 1, a guide rail 30 may be mounted to the ceiling of an examination room in which the X-ray imaging apparatus 1 is installed. An X-ray source 80 may be connected to a moving carriage 40 movable along the guide rail 30, such that the X-ray source 80 may be movable to a certain position corresponding to a target object P.

The moving carriage 40 is disposed at the lower side of the guide rail 30 so that the moving carriage 40 is movable along the guide rail 30. At the moving carriage 40 may be disposed a roller movable along the guide rail 30. The moving carriage 40 is movable in the first direction D1 and in the second direction D2 along the guide rail 30.

The moving carriage 40 may be connected to the X-ray source 80 through a bendable post frame 50, such that the height of the X-ray source 80 can be adjusted along a third direction D3.

A rotary joint 60 may be disposed between the X-ray source and the post frame 50. The rotary joint 60 may include a first rotary joint 61 connected to the post frame 50 and a second rotary joint 62 connected to the X-ray source 80.

The first rotary joint 61 may rotate in a fourth direction D4, and the second rotary joint 62 may rotate in a fifth direction D5. If the second rotary joint 62 rotates in a fifth direction D5, a tilt angle or rotation angle of the X-ray source 80 may be adjusted.

The X-ray source 80 may be automatically or manually movable. If the X-ray source 80 automatically moves, the X-ray imaging apparatus 1 may further include a driver, such as a motor, to provide the X-ray source 80 with drive power.

A workstation 90 may be disposed in the space isolated from the space including the X-ray source 80 through a shielding film B. The workstation 90 may include an input unit 92 configured to receive a command from the user and a display 91 configured to display information thereon.

The input unit 92 may receive an imaging protocol, an X-ray emission condition, an X-ray emission time point, and other commands needed for position control, point of interest (POI) region setting, etc. of the X-ray source 80 as input signals. The input unit 92 may include a keyboard, a mouse, a touch panel, a voice recognizer, a microphone, etc. The input unit 92 implemented as a touch panel may be disposed at the front of the display 91, resulting in formation of a touchscreen.

The display 91 may display an X-ray image, a camera image, a screen image for guiding the user to input a command, and a status image for displaying status information of the X-ray imaging apparatus 1.

The X-ray detector 100 may be mounted to a mounting part 14 or 24 provided in a table 10 or a stand 20, respectively, or may be implemented as a portable X-ray detector capable of being made available at any arbitrary position.

In a table mode, the X-ray detector 100 may be installed to the mounting part 14 of the table 10, such that the X-ray detector 100 may perform X-ray imaging of the target object P lied down on the table 10. In a stand mode, the X-ray detector 100 may be installed to the mounting part 24 of the stand 20, such that the X-ray detector 100 may perform X-ray imaging of the target object P who stands in front of the stand 20.

In a portable mode, the X-ray detector 100 is not installed to the mounting part 14 or 24 and may be located behind a region of the target object P, the X-ray detector 100 may perform X-ray imaging of the region of the target object P.

The X-ray detector 100 may be used as a constituent element of the X-ray imaging apparatus 1, or may not be included in the X-ray imaging apparatus. In the latter case, the X-ray detector 100 may be registered in the X-ray imaging apparatus 1 by a user or administrator. In addition, not only in the former case, but also in the latter case, X-ray images acquired by the X-ray detector 100 detecting X-rays may be transferred to the workstation 90.

Figure 2:
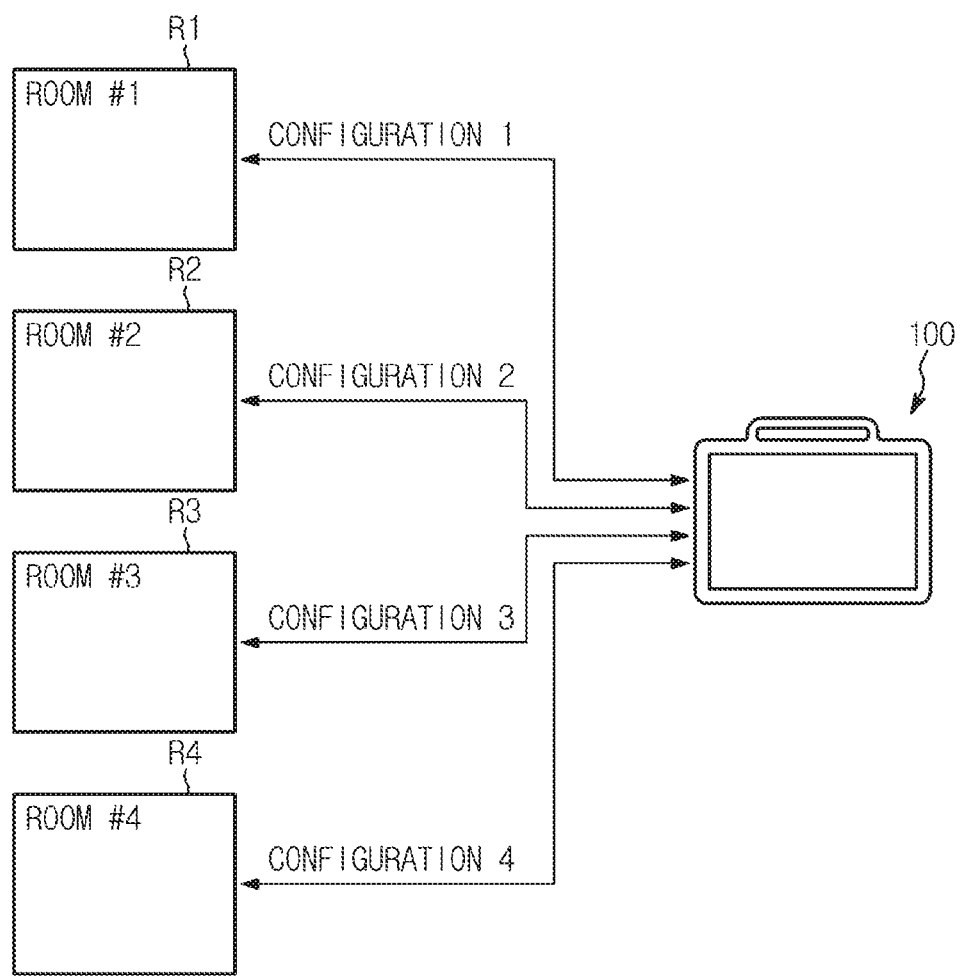
FIG. 2 is a conceptual diagram illustrating an exemplary case in which one X-ray detector is used in a plurality of imaging rooms.

FIG. 2 is a conceptual diagram illustrating an exemplary case in which only one X-ray detector is used in a plurality of imaging rooms.

Referring to FIG. 2, the X-ray detector 100 may be implemented as a portable product capable of being easily carried by the user, without being fixed to the mounting part 14 or 24 of the X-ray imaging apparatus 1, such that only one X-ray detector 100 may be shared by a plurality of imaging rooms R1, R2, R3, and R4 as shown in FIG. 2. The following embodiment describes an exemplary case in which four imaging rooms R1, R2, R3, and R4 share only one X-ray detector 100 for convenience of description, but a number of rooms can be 2, 3, . . . 10, . . . , 20, etc.

The X-ray imaging apparatus 1 may be installed in each of the imaging rooms. In order to use the X-ray detector 100, communication connection or network connection needs to be first implemented in a manner that the workstation 90 installed in the corresponding imaging room can communicate with the X-ray detector 100 through the communication or network connection.

In order to use the X-ray detector 100 within a first imaging room R1, a configuration (hereinafter referred to as first configuration "Configuration 1") needs to be established for allowing the workstation 90 installed in the first imaging room R1 to communicate with the X-ray detector 100. In order to use the X-ray detector 100 within a second imaging room R2, a configuration (hereinafter referred to as second configuration "Configuration 2") needs to be established for allowing the workstation 90 installed in the second imaging room R2 to communicate with the X-ray detector 100.

In order to use the X-ray detector 100 within a third imaging room R3, a configuration (hereinafter referred to as third configuration "Configuration 3") needs to be established for allowing the workstation 90 installed in the third imaging room R3 to communicate with the X-ray detector 100. In order to use the X-ray detector 100 within a fourth imaging room R4, a configuration (hereinafter referred to fourth configuration "Configuration 4") needs to be established for allowing the workstation 90 installed in the fourth imaging room R4 to communicate with the X-ray detector 100.

In the related art, communication between the X-ray detector and a workstation is implemented manually by the user who needs to directly input configuration information for Configuration 1, configuration information for Configuration 2, configuration information for Configuration 3, or configuration information for Configuration 4 whenever an imaging room to be used for X-ray imaging is changed to another imaging room. However, the X-ray detector 100, according to an embodiment, automatically implements communication between the X-ray detector 100 and a workstation by detecting the presence or absence of a specific event, such that the X-ray detector 100, according to an embodiment, increases user convenience, configuration accuracy, and/or a workflow of the hospital or an imaging facility.

Figure 3:
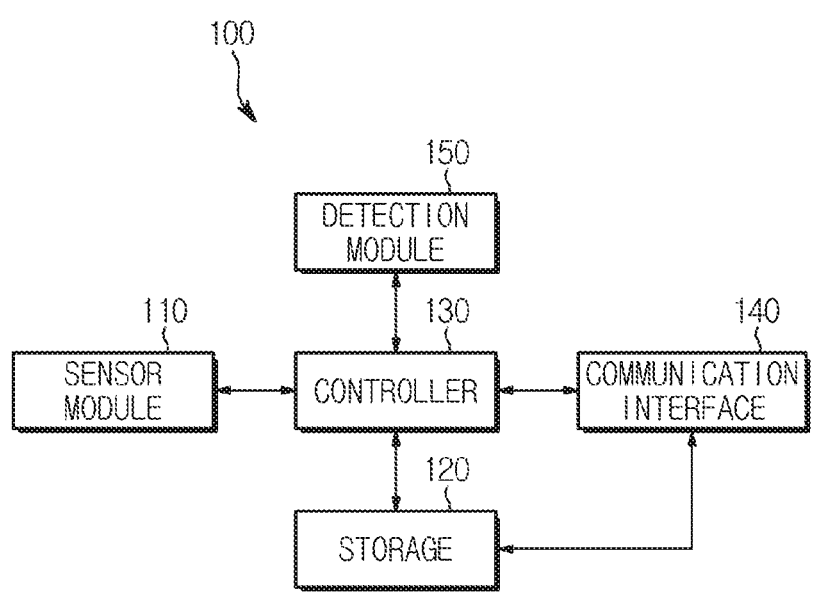
FIG. 3 is a block diagram illustrating an X-ray detector according to an embodiment.
Figure 4:
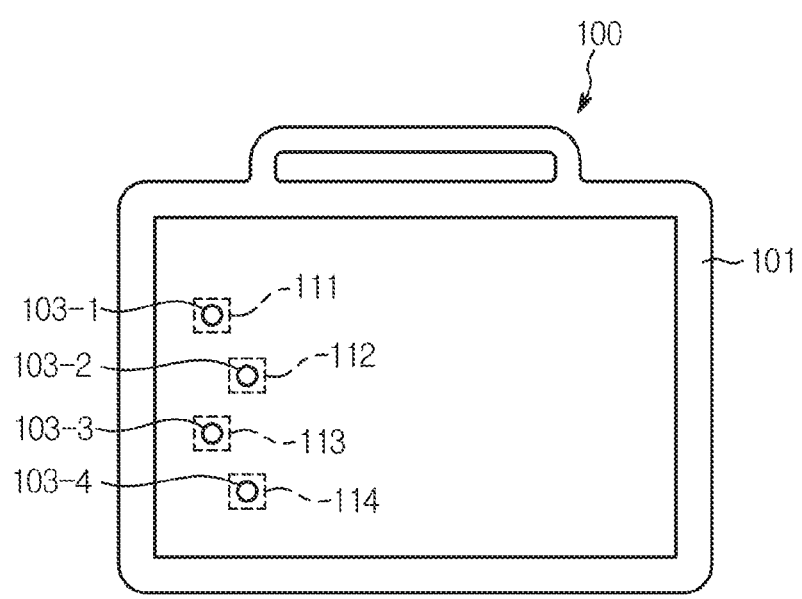
FIG. 4 is a view illustrating the external appearance of an X-ray detector according to an embodiment.

FIG. 3 is a block diagram illustrating an X-ray detector according to an embodiment. FIG. 4 is a view illustrating the external appearance of the X-ray detector according to an embodiment.

Referring to FIG. 3, the X-ray detector 100 may include a sensor module 110, e.g., sensor assembly, a storage 120, a communication interface 140, a controller 130, e.g., at least one processor or a microprocessor, and a detection module 150. The sensor module 110 may detect the presence or absence of an event. The storage 120 may match configuration information needed for communication with the workstation to respective predefined events, and may store the matched information therein. The communication interface 140 may communicate with an external device through wireless communication. If any one of the predefined events is detected, the controller 130 may perform configuration of the communication interface 140 using configuration information corresponding to the detected event. The detection module 150 may detect X-rays.

The sensor module 110 may include at least one of a magnetic sensor, an optical sensor, an IR sensor, an ultrasonic sensor, an acceleration sensor, a touch sensor, a gyro sensor, and a temperature sensor. If the sensor module 110 includes a plurality of sensors, the plurality of sensors may include only one kind of sensors, or different kinds of sensors.

If the sensor module 110 includes a magnetic sensor, an event detected by the sensor module 110 may include occurrence of a magnetic field. If the sensor module 110 includes an optical sensor, an IR sensor, and/or an ultrasonic sensor, an event to be detected by the sensor module 110 may include the presence or absence of an approaching object. If the sensor module 110 includes a touch sensor, an event to be detected by the sensor module 110 may include information about contact or non-contact of the object.

If the sensor module 110 includes a gyro sensor or an acceleration sensor, an event to be detected by the sensor module 110 may include information about rotation movement or rectilinear movement of the X-ray detector 100. If the sensor module 110 includes a temperature sensor, an event to be detected by the sensor module 110 may include information about change in temperature.

For example, the sensor module 110 may include as many sensors as the number of imaging rooms, the number of APs, or the number of workstations.

The sensor module 110 may include only one sensor, and different events corresponding to different imaging rooms, different events corresponding to different APs, or different events corresponding to different workstations may be matched to only one sensor.

The sensor module 110 may be embedded in the X-ray detector 100 or may be fabricated to be disposed outside.

For example, if the sensor contained in the sensor module 110 is at least one of the magnetic sensor, the acceleration sensor, the gyro sensor, and the temperature sensor, this sensor module 110 may be embedded in the X-ray detector 100.

If the sensor contained in the sensor module 110 is at least one of the optical sensor, the ultrasonic sensor, and the touch sensor, this sensor module 110 may be fabricated to be exposed outside the X-ray detector 100. If the housing of the X-ray detector 100 is formed of a transparent material, this sensor module 110 may be provided in the transparent housing.

As shown in FIG. 4, if the sensor module 110 is embedded in the X-ray detector 100, markers 103-1, 103-2, 103-3, and 103-4, each of which indicating the position of the sensor, may be provided on the housing 101 of the X-ray detector 100.

For example, if the sensor module 110 includes four sensors, i.e., first through fourth sensors 111, 112, 113, and 114, markers 103-1, 103-2, 103-3, and 103-4 may be provided at the positions corresponding to the respective sensors.

The markers 103-1, 103-2, 103-3, and 103-4 may be engraved or embossed in the housing 101, may be attached to the surface of the housing 101, or may be printed on the surface of the housing 101. In this way, the markers 103-1, 103-2, 103-3, and 103-4 may indicate the position of each sensor, and there is no limitation in categories of the markers 103-1, 103-2, 103-3, and 103-4.

After the X-ray detector 100 has been manufactured and sold to customers, the markers 103-1, 103-2, 103-3, and 103-4 may be directly provided by an instruction of a user of the X-ray detector 100.

Referring back to FIG. 3, the storage 120 may match configuration information needed to establish communication with the workstation to the respective predefined events, and may store the matched information therein. In this case, the configuration information needed to establish communication with the workstation acting as a destination of such communication connection may include information about an AP connected to the workstation or ID information of the corresponding workstation. The AP information may include wireless AP (WAP) configuration data, and the WAP configuration data may include at least one of a Service Set Identifier (SSID), an Internet (IP) address, a passphrase, a country code, etc.

The workstation ID information may include at least one of an IP address, a Media Access Control (MAC) address, etc.

The storage 120 may include a non-volatile memory, such as a read only memory (ROM), a flash memory, a hard disc, or an optical disc drive, and/or a volatile memory, such as a Static Random Access memory (SRAM) or a Dynamic Random Access Memory (DRAM).

The communication interface 140 may communicate with the workstation 90 through wireless communication. For example, the communication interface 140 may receive an X-ray emission ready signal from the workstation 90, and may transmit X-ray imaging signals acquired by the detection module 150 detecting X-rays to the workstation 90.

The communication interface 140 may include a wireless communication interface and/or a wired interface to communicate wirelessly and/or by wires with the various components and/or devices. For example, the communication interface 140 may include a connector, a plug, a processor, a microprocessor, a transceiver, and/or an antenna, etc. For example, the communication interface 140 may include at least one of various wireless communication interfaces based on Wireless Local Access Network (WLAN), Wireless Fidelity (Wi-Fi), Wireless Broadband (WiBro), Global System for Mobile Communication (GSM), Code Division Multiple Access (CDMA), Wideband Code Division Multiple Access (WCDMA), Universal Mobile Telecommunications System (UMTS), Time Division Multiple Access (TDMA), Long Term Evolution (LTE), 4G communication, 5G communication, etc.

In order to allow the communication interface 140 to communicate with a specific external device, the communication interface 140 needs to perform a configuration action to implement communication with the specific external device. In the following embodiment, the configuration action may be a network configuration.

The controller 130 may determine whether the sensor module 110 has detected any of the predefined events. For this purpose, an output value of the sensor module 110 may be transmitted to the controller 130. The output value of the sensor module 110 may be transmitted to the controller 130 in real time or periodically. If there is a change in output values of the sensor module 110, i.e., if the sensor module 110 detects any of the new events, the changed output value may be transmitted to the controller 130 upon detection or as defined by a user.

The controller 130 may determine whether the predefined event has occurred based on the output value of the sensor module 110. If the controller 130 determines occurrence of the predefined event, i.e., if the sensor module 110 detects the predefined event, configuration information corresponding to the detected event may be searched for in the storage 120, such that the retrieved configuration information can be acquired from the storage 120. If the configuration information corresponding to the detected event has been acquired, the controller 130 may perform network configuration of the communication interface 140 based on the acquired configuration information.

The controller 130 may control overall operation of the X-ray detector 100. For example, upon receiving an X-ray emission ready signal from the workstation 90 connected to the communication interface 140, the controller 130 may control the detection module 150 to enter a ready status in which the detection module 150 can detect X-rays. If the detection module 150 detects an X-ray imaging signal by detecting X-rays, the detection module 150 may transmit the detected X-ray imaging signal to the workstation 90 through the communication interface 140.

The controller 130 may use the storage 120 and/or include at least one memory to store programs needed for the aforementioned operations or other operations, and may include at least one processor to execute the stored programs.

The detection module 150 may be classified according to a scheme for converting the detected X-rays into an electrical signal and a scheme for obtaining the electrical signal. The scheme for converting X-rays into the electrical signal may be a direct conversion scheme and an indirect conversion scheme.

Additionally, according to a method of obtaining electrical signals, the detection module 150 may be classified into a charge integration mode in which charges are stored for a certain time and then signals are obtained, and a photon counting mode in which photons having energy greater than threshold energy are counted whenever signals are generated by a single X-ray photon. During the photon counting mode, the target object can be imaged with a lower dose (i.e., a smaller number of X-ray photons), and a superior signal-to-noise ratio (SNR) image can be obtained. On the other hand, X-ray flux detectable by the detection module 150 in the charge integration mode may be higher than X-ray flux detectable by the detection module 150 in the photon counting mode. That is, a saturation level and a dynamic range for use in the charge integration mode may be higher than a saturation level and a dynamic range for use in the photon counting mode.

In the direct conversion mode, if X-rays are irradiated, electron-hole pairs may be temporarily generated in a light receiving element of the detection module 150, and the electrons move to an anode and the holes move to a cathode by an electric field applied to both ends of the light receiving element, such that detection elements may convert such movement into electrical signals. In the direct conversion mode, a material used for the light receiving element may include a-Se, CdZnTe, $HgI_2$, $PbI_2$ or the like.

In the indirect conversion mode, a scintillator may be provided over the detection module 150. X-rays irradiated from the X-ray source 80 react with a scintillator and photons having a wavelength of visible light are emitted. The light receiving element detects the photons and converts the same into electrical signals. In the indirect conversion mode, a material used for the light receiving element may include a-Si or the like, and the scintillator may be embodied as a thin-film type GADOX scintillator, or a micro-column type or needle structured type CsI (T1) scintillator.

The detection module 150 may be implemented using any of the direct conversion mode, the indirect conversion mode, the charge integration mode, and the photon counting mode. All kinds of the direct conversion mode, the indirect conversion mode, the charge integration mode, and the photon counting mode can be applied to the detection module 150 without departing from the scope or spirit of the disclosure.

FIG. 5 is a conceptual diagram illustrating one example of information stored in the storage of the X-ray detector according to an embodiment. FIGS. 6A to 6D illustrate an example of network configuration that is performed in response to an event generated in the sensor module of the X-ray detector according to an embodiment.

Referring to FIG. 5, the storage 120 may perform matching of AP information to be used in network configuration for each sensor having detected the predefined event, and may store the matched information therein. For example, WAP #1 configuration data to be connected to a first AP (AP 1) may be matched to a first sensor 111 among four sensors contained in the sensor module 110, and the matched information may be stored in the storage 120. WAP #2 configuration data to be connected to a second AP (AP 2) may be matched to a second sensor 112 among the four sensors, and the matched information may be stored in the storage 120. WAP #3 configuration data to be connected to a third AP (AP 3) may be matched to a third sensor 113 among the four sensors, and the matched information may be stored in the storage 120. WAP #4 configuration data to be connected to a fourth AP (AP 4) may be matched to a fourth sensor 114 among the four sensors, and the matched information may be stored in the storage 120.

Information to be stored in the storage 120 may be input to the storage 120 by the user or an installation engineer during installation of the X-ray detector 100.

If the predefined event occurs in at least one of the four sensors contained in the sensor module 110, AP information corresponding to the sensor in which the event has occurred may be searched for in the storage 120, and may be acquired from the storage 120. Network configuration of the communication interface 140 may be carried out based on the acquired AP information.

For example, if the sensor module 110 includes a magnetic sensor, the sensor module 110 may detect occurrence of a magnetic field. The user may generate an event in the sensor module 110 using a magnet configured to generate a magnetic field having predetermined intensity. The controller 130 may preset the intensity of a magnetic field generated by the corresponding magnet to a reference value. If the sensor module 110 detects a magnetic field that is equal to or higher than the reference value, i.e., if the output value of the sensor module 110 is equal to or higher than the reference value, the controller 130 may determine that the predefined event has occurred.

The user may be apprised of the event corresponding to either the AP or the workstation to be connected to the X-ray detector 100, and may perform operation needed to the corresponding event. For example, if the predefined event indicates a specific event generated in the sensor allocated to each AP or each workstation, the user may generate the specific event in the sensor allocated to the AP or workstation of the imaging room in which the X-ray detector 100 is scheduled to be used.

Figure 6A:
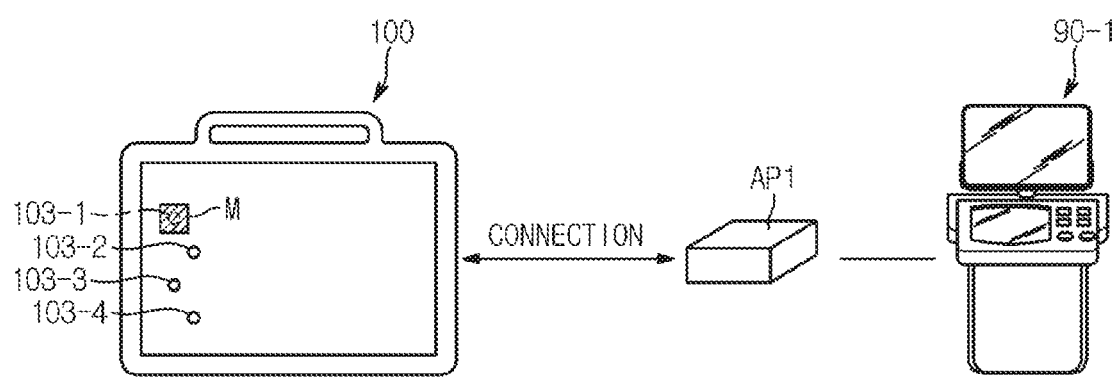
FIGS. 6A, 6B, 6C, and 6D illustrate an example of network configuration according to an embodiment.

Referring to FIG. 6A, if the user moves the magnet M toward the first sensor 111, for example, if the user places the magnet M over a first marker 103-1 corresponding to the first sensor 111, the controller 130 may determine that the predefined event has occurred in the first sensor 111 among the plurality of sensors contained in the sensor module 110.

The controller 130 may search for AP information corresponding to the first sensor 111 in the storage 120, and may acquire the retrieved AP information from the storage 120. If the same information as in FIG. 5 is stored in the storage 120, the controller 130 may acquire WAP #1 configuration data to be connected to the first AP (AP1), and may perform network configuration of the communication interface 140 using the WAP #1 configuration data.

If such network configuration is completed, the communication interface 140 may be connected to the first workstation 90-1 through the first AP (AP 1). For example, if the first AP (AP 1) is installed in a first imaging room R1, the X-ray detector 100 may be made available in the first imaging room R1.

Figure 6B:
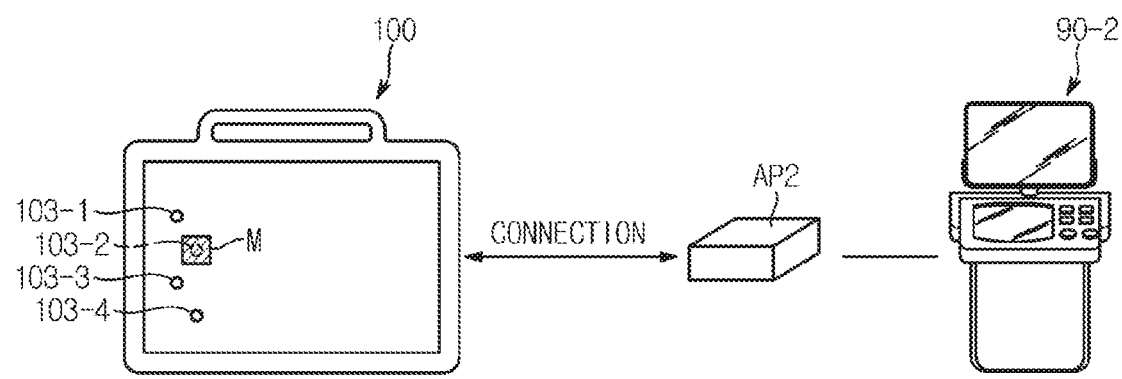

In FIG. 6B, if the user moves the magnet M toward the second sensor 112, for example, if the user places the magnet M over a second marker 103-2 corresponding to the second sensor 112, the controller 130 may determine that the predefined event has occurred in the second sensor 112 among the plurality of sensors contained in the sensor module 110.

The controller 130 may search for AP information corresponding to the second sensor 112 in the storage 120, and may acquire the retrieved AP information from the storage 120. If the same information as in FIG. 5 is stored in the storage 120, the controller 130 may acquire WAP #2 configuration data to be connected to the second AP (AP2), and may perform network configuration of the communication interface 140 using the WAP #2 configuration data.

If such network configuration is completed, the communication interface 140 may be connected to the second workstation 90-2 through the second AP (AP 2). For example, if the second AP (AP 2) is installed in a second imaging room R2, the X-ray detector 100 may be made available in the second imaging room R2.

Figure 6C:
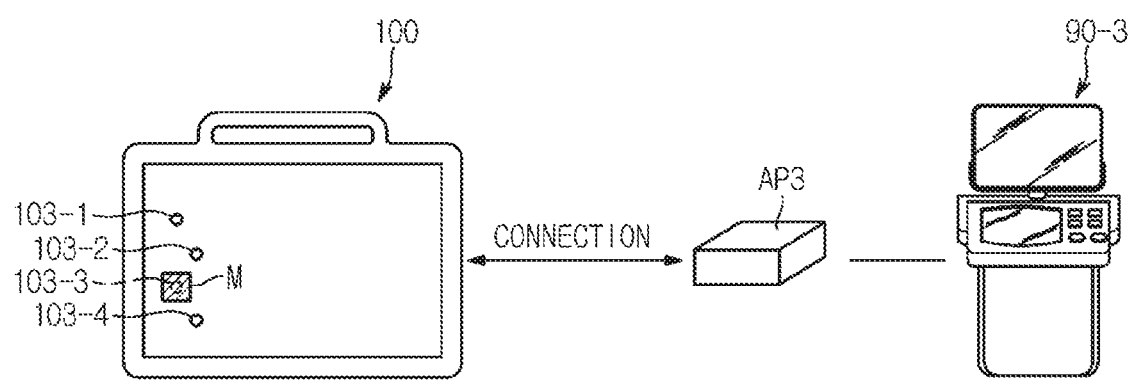

In FIG. 6C, if the user moves the magnet M toward the third sensor 113, for example, if the user places the magnet M over a third marker 103-3 corresponding to the third sensor 113, the controller 130 may determine that the predefined event has occurred in the third sensor 113 among the plurality of sensors contained in the sensor module 110.

The controller 130 may search for AP information corresponding to the third sensor 113 in the storage 120, and may acquire the retrieved AP information from the storage 120. If the same information as in FIG. 5 is stored in the storage 120, the controller 130 may acquire WAP #3 configuration data to be connected to the third AP (AP3), and may perform network configuration of the communication interface 140 using the WAP #3 configuration data.

If such network configuration is completed, the communication interface 140 may be connected to the third workstation 90-3 through the third AP (AP 3). For example, if the third AP (AP 3) is installed in a third imaging room R3, the X-ray detector 100 may be made available in the third imaging room R3.

Figure 6D:
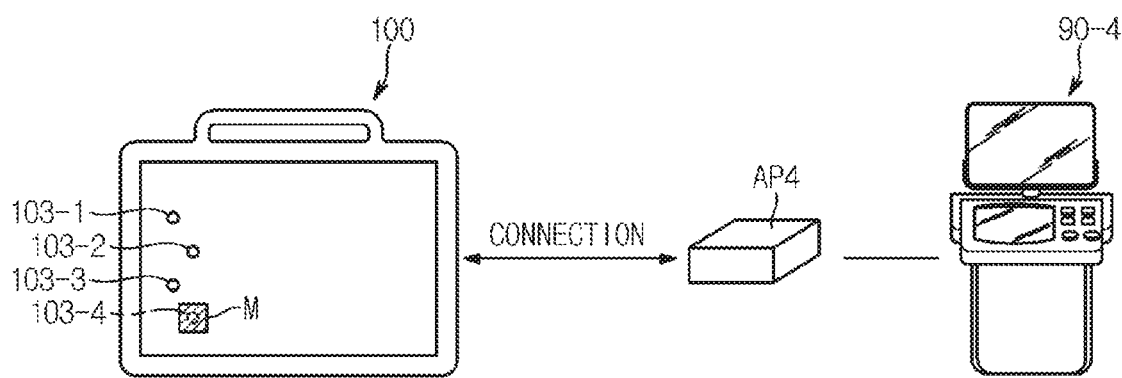

In FIG. 6D, if the user moves the magnet M toward the fourth sensor 114, for example, if the user places the magnet M over a fourth marker 103-4 corresponding to the fourth sensor 114, the controller 130 may determine that the predefined event has occurred in the fourth sensor 114 among the plurality of sensors contained in the sensor module 110.

The controller 130 may search for AP information corresponding to the fourth sensor 114 in the storage 120, and may acquire the retrieved AP information from the storage 120. If the same information as in FIG. 5 is stored in the storage 120, the controller 130 may acquire WAP #4 configuration data to be connected to the fourth AP (AP4), and may perform network configuration of the communication interface 140 using the WAP #4 configuration data.

If such network configuration is completed, the communication interface 140 may be connected to the fourth workstation 90-4 through the fourth AP (AP 4). For example, if the fourth AP (AP 4) is installed in a fourth imaging room R4, the X-ray detector 100 may be made available in the fourth imaging room R4.

FIG. 7 is a conceptual diagram illustrating an example of information stored in the storage of the X-ray detector according to an embodiment. FIGS. 8A to 8D illustrate an example of network configuration that is performed in response to an event generated in the sensor module of the X-ray detector according to an embodiment.

In accordance with the embodiments, the access point AP may be embedded in the X-ray detector 100. Alternatively, in the same manner as in Wi-Fi Direct (WFD), one selected among the access point AP and the X-ray detector 100 may act as a master and the remaining one may act as a slave, such that the AP and the X-ray detector 100 may communicate with each other.

In this case, as shown in FIG. 7, the storage 120 may directly match each sensor in which the predefined event has occurred to workstation information to be used for network configuration, and may store the matched information therein.

For example, ID information of the first workstation 90-1 may be matched to the first sensor 111 among the four sensors contained in the sensor module 110, and the matched information may be stored in the storage 120. ID information of the second workstation 90-2 may be matched to the second sensor 112, and the matched information may be stored in the storage 120. ID information of the third workstation 90-3 may be matched to the third sensor 113, and the matched information may be stored in the storage 120. ID information of the fourth workstation 90-4 may be matched to the fourth sensor 114, and the matched information may be stored in the storage 120.

If at least one of the four sensors contained in the sensor module 110 detects the predefined event, the controller 130 may search for workstation information corresponding to the sensor having detected the predefined event in the storage 120, and may acquire the retrieved workstation information from the storage 120. The controller 130 may perform network configuration of the communication interface 140 based on the acquired workstation information.

Figure 8A:
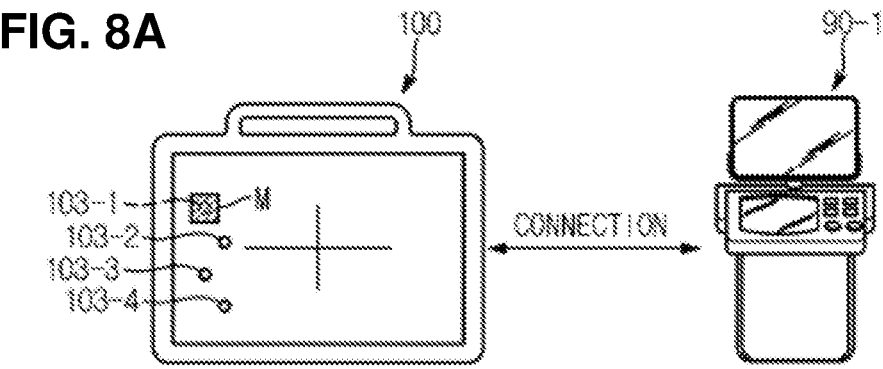
FIGS. 8A, 8B, 8C, and 8D illustrate an example of network configuration according to an embodiment.

Referring to FIG. 8A, if the user moves the magnet M toward the first sensor 111, the controller 130 may determine that the predefined event has occurred in the first sensor 111 among the plurality of sensors contained in the sensor module 110.

The controller 130 may search for workstation information corresponding to the first sensor 111 in the storage 120. If the same information as in FIG. 7 is stored in the storage 120, the controller 130 may perform network configuration of the communication interface 140 using ID information of the first workstation 90-1. If network configuration is completed, the communication interface 140 may be directly coupled to the first workstation 90-1.

Figure 8B:
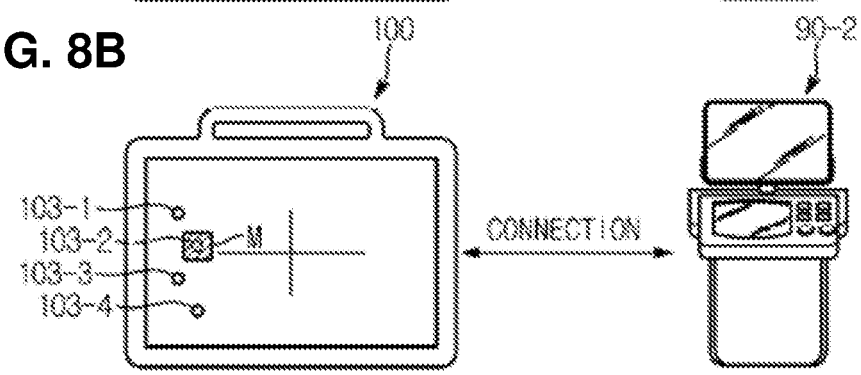

In FIG. 8B, if the user moves the magnet M toward the second sensor 112, the controller 130 may determine that the predefined event has occurred in the second sensor 112 among the plurality of sensors contained in the sensor module 110.

The controller 130 may search for workstation information corresponding to the second sensor 112 in the storage 120. If the same information as in FIG. 7 is stored in the storage 120, the controller 130 may perform network configuration of the communication interface 140 using ID information of the second workstation 90-2. If network configuration is completed, the communication interface 140 may be directly coupled to the second workstation 90-2.

Figure 8C:
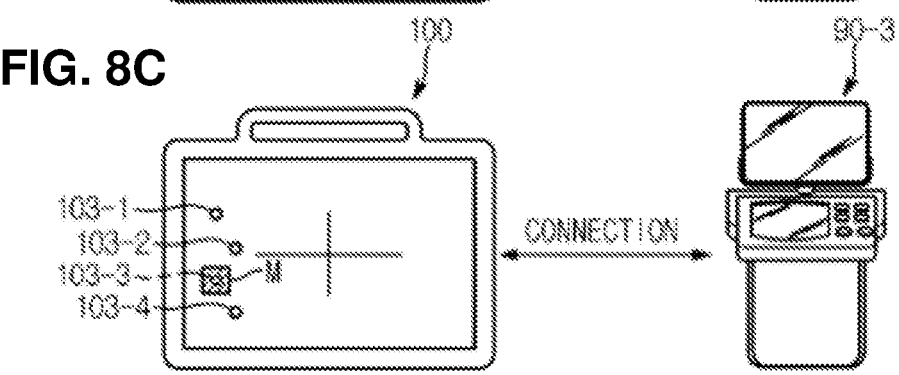

In FIG. 8C, if the user moves the magnet M toward the third sensor 113, the controller 130 may determine that the predefined event has occurred in the third sensor 113 among the plurality of sensors contained in the sensor module 110.

The controller 130 may search for workstation information corresponding to the third sensor 113 in the storage 120. If the same information as in FIG. 7 is stored in the storage 120, the controller 130 may perform network configuration of the communication interface 140 using ID information of the third workstation 90-3. If network configuration is completed, the communication interface 140 may be directly coupled to the third workstation 90-3.

Figure 8D:
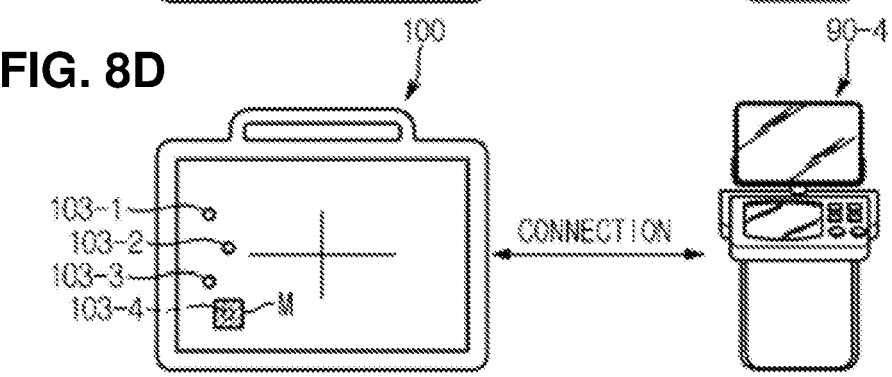

In FIG. 8D, if the user moves the magnet M toward the fourth sensor 114, the controller 130 may determine that the predefined event has occurred in the fourth sensor 114 among the plurality of sensors contained in the sensor module 110.

The controller 130 may search for workstation information corresponding to the fourth sensor 114 in the storage 120. If the same information as in FIG. 7 is stored in the storage 120, the controller 130 may perform network configuration of the communication interface 140 using ID information of the fourth workstation 90-4. If network configuration is completed, the communication interface 140 may be directly coupled to the fourth workstation 90-4.

Figure 9:
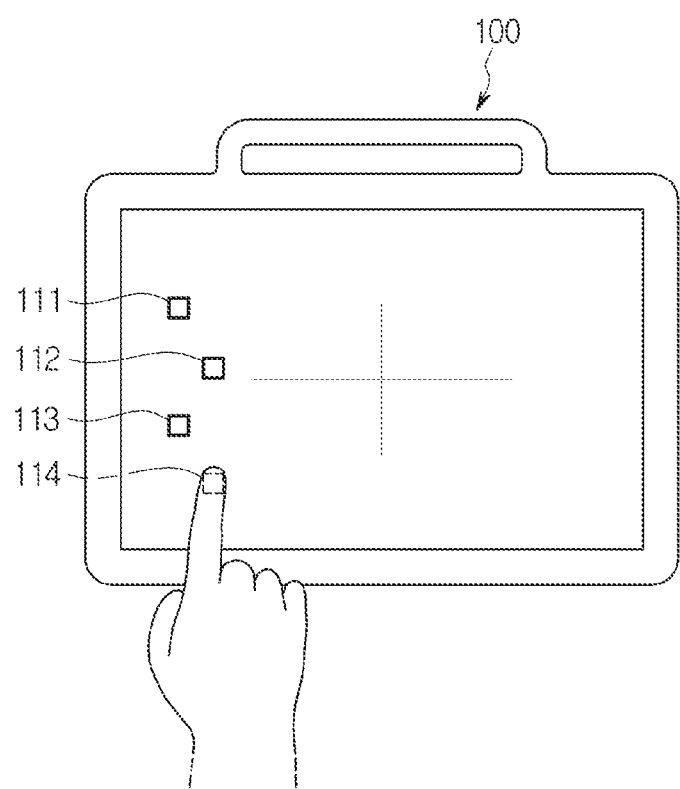
FIG. 9 is a view illustrating exemplary events detected by a sensor module of an X-ray detector according to an embodiment.

FIG. 9 is a view illustrating exemplary events detected by the sensor module of the X-ray detector according to an embodiment.

As described above, the sensor module 110 may include the magnetic sensor, the optical sensor, the ultrasonic sensor, a touch sensor, and/or the IR sensor, and the storage 120 may include the same information as described above with reference to FIGS. 5 and 7.

Referring to FIG. 9, the user may generate an event by touching the sensor 114 corresponding to the fourth workstation 90-4 to be connected to the X-ray detector 100. In this case, the output signal of the sensor touched by the user may be set to a reference value by the controller 130. If the sensor module 110 outputs a sensor output value that is equal to or higher than the reference value or another sensor value that is less than the reference value, the controller 130 may determine that the predefined event has occurred. The sensor output value of the sensor module 110 may be established in different ways according to the categories of the sensors.

In the above-described example, the sensor module 110 includes the plurality of sensors allocated to each AP or each workstation, and the predefined event indicates a specific event generated in the sensor allocated to each AP or each workstation.

In another example, the sensor module 110 may include only one sensor, and may allow the respective APs or workstations to have different types of events or different numbers of events, such that it may be possible to discriminate between the APs to be connected to the X-ray detector 100 or it may be possible to discriminate between the workstations to be connected to the X-ray detector 100.

Figure 10:
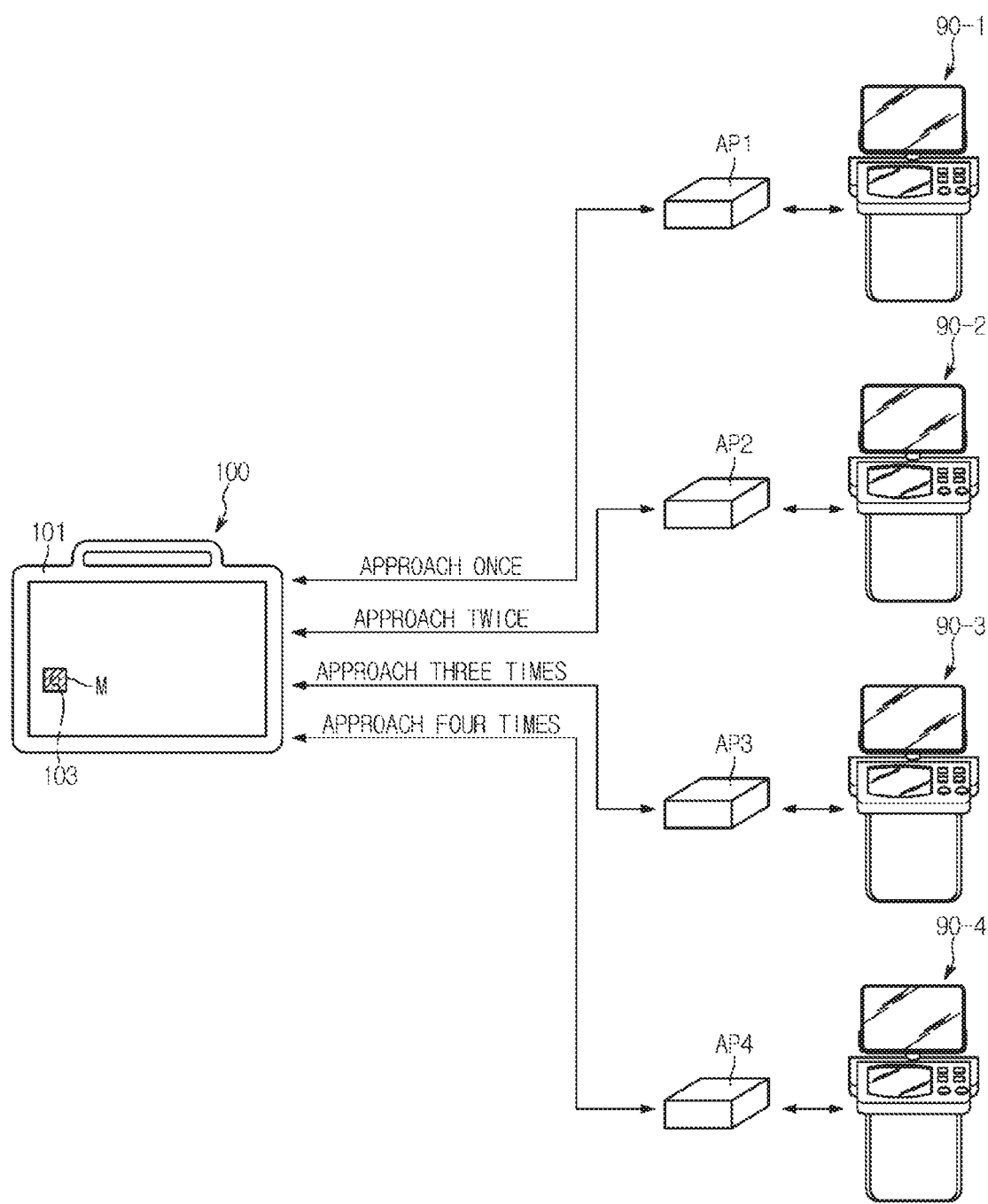
FIG. 10 is a conceptual diagram illustrating examples of events generated in a magnetic sensor according to an embodiment.
Figure 11:
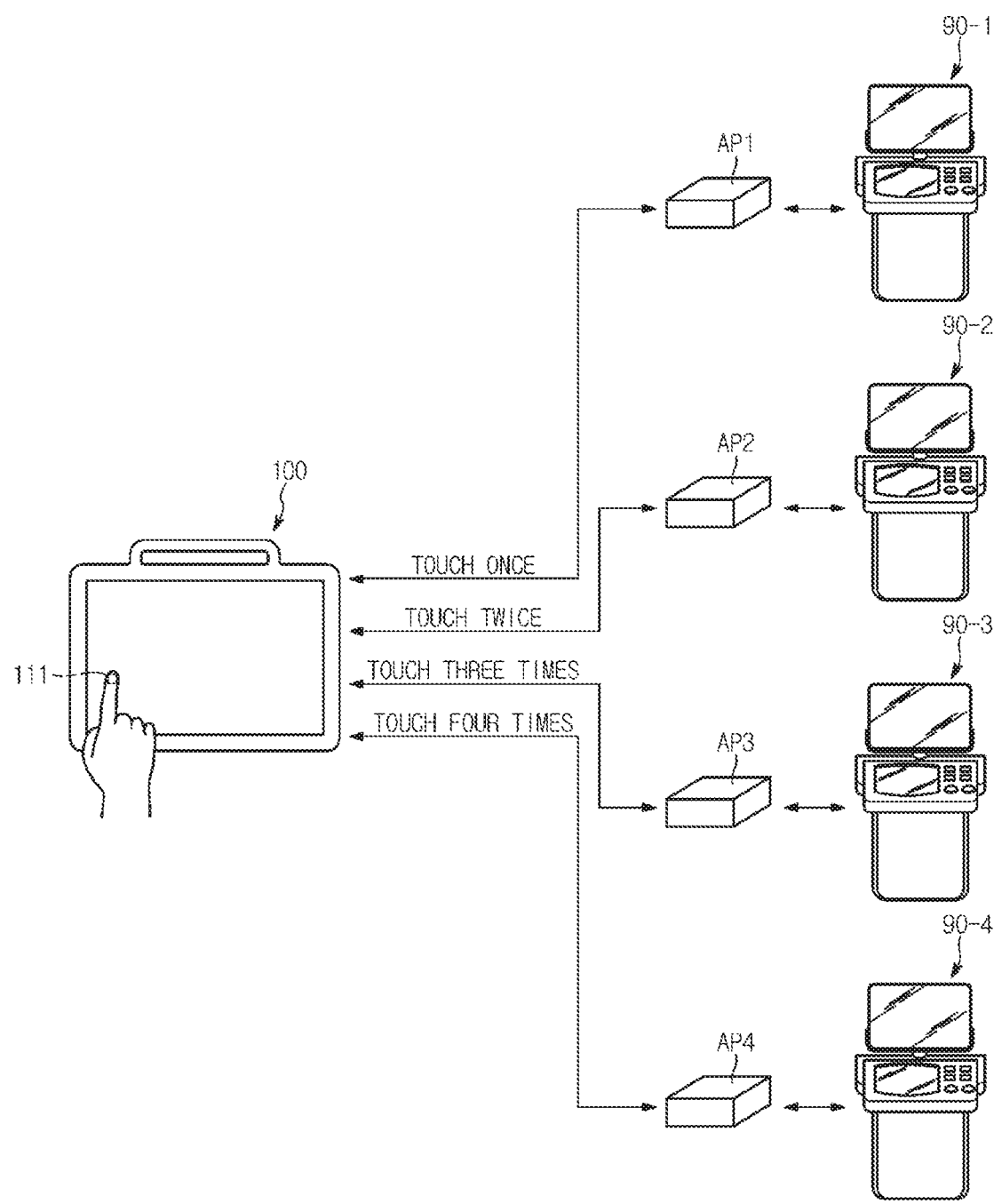
FIG. 11 is a conceptual diagram illustrating example of events generated in a touch sensor according to an embodiment.

FIG. 10 is a conceptual diagram illustrating examples of events generated in a single magnetic sensor according to an embodiment. FIG. 11 is a conceptual diagram illustrating example of events generated in the single touch sensor according to an embodiment.

Referring to FIG. 10, the sensor module 110 may include only one magnetic sensor. The marker 103 indicating the position of only one magnetic sensor may be formed in the housing 101 of the X-ray detector 100.

For example, the respective events to be matched to the plurality of APs or the plurality of workstations may be distinguished from each other according to information about how many times the magnet M approaches the magnetic sensor, and the events capable of being identified according to the number of approach times of the magnet M may be stored in the storage 120.

In more detail, if the magnet M approaches the magnetic sensor once, the controller 130 may search for configuration information needed for connection to the first access point AP1 in the storage 120, and the configuration information may be acquired from the storage 120. The controller 130 may perform network configuration of the communication interface 140 using the acquired configuration information.

If network configuration is completed, the communication interface 140 may be connected to the first workstation 90-1 through the first access point AP1.

If the magnet M approaches the magnetic sensor twice, the controller 130 may search for configuration information needed for connection to the second access point AP2 in the storage 120, and the configuration information may be acquired from the storage 120. The controller 130 may perform network configuration of the, communication interface 140 using the acquired configuration information. If network configuration is completed, the communication interface 140 may be connected to the second workstation 90-2 through the second access point AP2.

If the magnet M approaches the magnetic sensor three times, the controller 130 may search for configuration information needed for connection to the third access point AP3 in the storage 120, and the configuration information may be acquired from the storage 120. The controller 130 may perform network configuration of the communication interface 140 using the acquired configuration information. If network configuration is completed, the communication interface 140 may be connected to the third workstation 90-3 through the third access point AP3.

If the magnet M approaches the magnetic sensor four times, the controller 130 may search for configuration information needed for connection to the fourth access point AP4 in the storage 120, and the configuration information may be acquired from the storage 120. The controller 130 may perform network configuration of the communication interface 140 using the acquired configuration information. If network configuration is completed, the communication interface 140 may be connected to the fourth workstation 90-4 through the fourth access point AP4.

Referring to FIG. 11, if the sensor module 110 includes only one touch sensor, for example, the first sensor 111, the respective events corresponding to the plurality of APs or the plurality of workstations may be identified from each other according to information about how many times the user touches the touch sensor. For example, the user may touch a particular position on the X-ray detector identified by a marker, a graphics, etc., or a user's touch on any position on a surface of the X-ray detector may be determined as a user input corresponding to an event. The respective events capable of being identified from each other according to the number of user touch actions may be stored in the storage 120.

In more detail, if the user touches the touch sensor once, the controller 130 may search for configuration information needed for connection to the first access point (AP1) in the storage 120, may acquire the retrieved configuration information from the storage 120, and may perform network configuration of the communication interface 140 using the acquired configuration information. If the network configuration is completed, the communication interface 140 may be connected to the first workstation 90-1 through the first access point (AP1).

If the user touches the touch sensor twice, the controller 130 may search for configuration information needed for connection to the second access point (AP2) in the storage 120, may acquire the retrieved configuration information from the storage 120, and may perform network configuration of the communication interface 140 using the acquired configuration information. If the network configuration is completed, the communication interface 140 may be connected to the second workstation 90-2 through the second access point (AP2).

If the user touches the touch sensor three times, the controller 130 may search for configuration information needed for connection to the third access point (AP3) in the storage 120, may acquire the retrieved configuration information from the storage 120, and may perform network configuration of the communication interface 140 using the acquired configuration information. If the network configuration is completed, the communication interface 140 may be connected to the third workstation 90-3 through the third access point (AP3).

If the user touches the touch sensor four times, the controller 130 may search for configuration information needed for connection to the fourth access point (AP4) in the storage 120, may acquire the retrieved configuration information from the storage 120, and may perform network configuration of the communication interface 140 using the acquired configuration information. If the network configuration is completed, the communication interface 140 may be connected to the fourth workstation 90-4 through the fourth access point (AP4).

Even when the sensor module 110 includes only one sensor, the sensor module 110 may be directly connected to the workstation 90 without passing through any AP. In this case, the same information as in FIG. 7 may be stored in the storage 120. The controller 130 may detect the category of the event detected by the sensor module 110, such that the controller 130 may perform network configuration needed for connection to the workstation appropriate for the detected event according to the detected event category.

Meanwhile, as shown in FIGS. 10 and 11, if the event to be allocated to each AP or each workstation is defined according to the number of occurrences of the same event, the number of the corresponding events may be counted during a predetermined time. For example, if the predetermined time is 10 seconds, the controller 130 may count how many times the magnet M approaches the magnetic sensor during 10 seconds, or may count how many times the user touches the touch sensor during 10 seconds, such that the controller 130 may determine which one of the events has occurred.

Alternatively, it may be possible to change network configuration whenever the event occurs. For example, if the magnet M approaches the magnetic sensor once, the controller 130 may perform network configuration needed for connection to the first access point (AP1). Thereafter, if the magnet M approaches the magnetic sensor once more, the controller 130 may change network configuration needed for connection to the second access point (AP2). As described above, if the numbers of approach times of the magnet M are accumulated, and if the magnet M approaches the magnet M once more, the controller 130 may change network configuration needed for connection to the third access point (AP3). Even when the sensor module 110 includes a touch sensor, an optical sensor, etc. therein, the sensor module 110 may operate in the same manner as in the above-described embodiment.

The controller 130 may perform network configuration according to the respective events detected by the sensor module 110, and may establish or set up a drive mode of the X-ray detector 100.

The storage 120 may match the drive modes to the predefined events, and may store the matched information therein. If it is determined that the sensor module 110 has detected the predefined event, the controller 130 may drive the X-ray detector 100 according to the respective drive modes corresponding to the predefined events. For example, the respective drive modes, i.e., an auto exposure detection (AED) mode, a sleep in/output mode, a fast scan mode, etc. may be matched to the respective predefined events, and the matched information may be stored in the storage 120.

The respective events stored in the storage 120 after being matched to the respective drive modes may be identical to or different from the events to be stored in network configuration. If the respective events are identical to the stored events, network configuration may first be carried out, and the drive modes may then be established. Alternatively, the drive modes may first be established, and network configuration may then be carried out.

For example, if the sensor module 110 includes the plurality of sensors, different drive modes may be matched to the respective sensors, and the controller 130 may establish the drive mode of the X-ray detector 100 according to the drive mode corresponding to the sensor having detected the predefined event.

Alternatively, it may be possible to establish the respective imaging modes of the X-ray detector 100 according to the respective events detected by the sensor module 110. The storage 120 may match the appropriate imaging modes to the respective predefined events, and may store the matched information therein. If the sensor module 110 has detected any one of the predefined events, the controller 130 may transmit information about the imaging mode corresponding to the detected event to the workstation 90 connected to the communication interface 140.

For example, if the sensor module 110 includes the plurality of sensors, different imaging modes (i.e., a stand mode, a table mode, a portable mode) may be matched to the respective sensors, and the controller 130 may transmit information about the imaging mode corresponding to the sensor having detected the predefined event to the workstation 90.

In more detail, if the sensor having detected the predefined event among the sensors of the sensor module 110 is a sensor corresponding to the portable mode, the controller 130 may transmit information indicating that the X-ray detector 100 is used as a portable X-ray detector to the workstation 90 through the communication interface 140.

As described above, AP information or workstation information corresponding to the respective predefined events may be stored in the storage 120. Communication connection to the AP matched to the event generated in the X-ray detector 100 or communication connection to the workstation matched to the event generated in the X-ray detector 100 may be automatically carried out. As a result, when only one X-ray detector is used in the plurality of imaging rooms or in the plurality of workstations, the user does not need to manually change network configuration to another whenever the imaging room or workstation in which the X-ray detector will be used is changed to another imaging room or another workstation such that user convenience is improved and the possibility of configuration errors caused by the user can be greatly reduced.

The above-described embodiments describe that only one X-ray detector 100 is used in the plurality of imaging rooms and/or with the plurality of workstations. The following embodiment describes an embodiment in which a plurality of X-ray detectors is used in one imaging room or with one workstation. However, the described above is applicable to one or more of the plurality of X-ray detectors described below.

Figure 12:
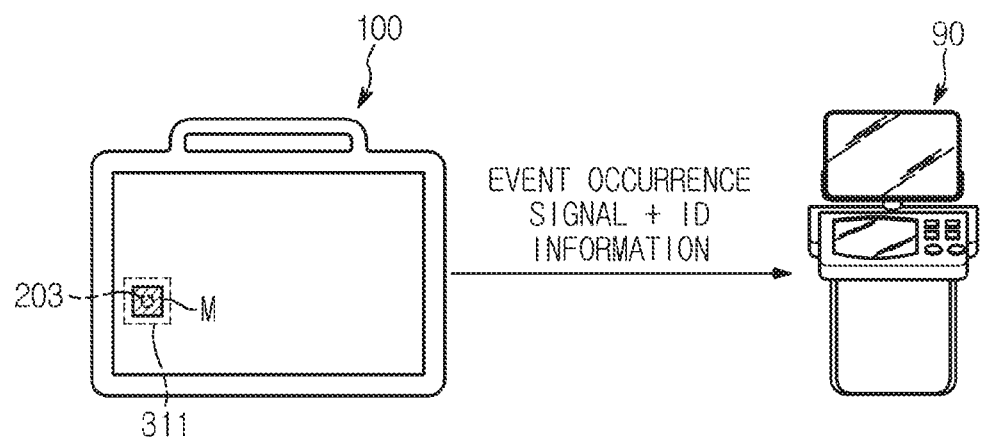
FIG. 12 is a conceptual diagram illustrating examples of network configuration according to an embodiment.

FIG. 12 is a conceptual diagram illustrating examples of network configuration that is performed in response to events generated in a sensor module of the X-ray detector 100 according to an embodiment.

For example, the controller 130 may determine whether the predefined event has occurred based on the output signal of the sensor module 110 and information stored in the storage 120. For example, if the sensor module 110 includes a magnetic sensor, and if the sensor module 110 detects a magnetic field that is equal to or higher than a predetermined reference value, the controller 130 may determine occurrence of the predefined event.

For example, the user may move the magnet M toward the position (marker 203) corresponding to the magnetic sensor of the X-ray detector 100 to be used for X-ray imaging.

If the predefined event has occurred, the controller 130 may transmit an event occurrence signal and ID information of the X-ray detector 100 to the workstation 90 connected to the communication interface 140 as shown in FIG. 12. The controller 130 may transmit the event occurrence signal and ID information of the X-ray detector 100 through the AP or may directly transmit the same to the workstation 90 according to communication methods between the communication interface 140 and the workstation 90.

The workstation 90 may recognize that the X-ray detector 100 in which the event has occurred among the plurality of X-ray detectors is scheduled to be used for X-ray imaging, and may perform various kinds of configuration actions to be used in the X-ray imaging operation of the corresponding X-ray detector 100.

Figure 13:
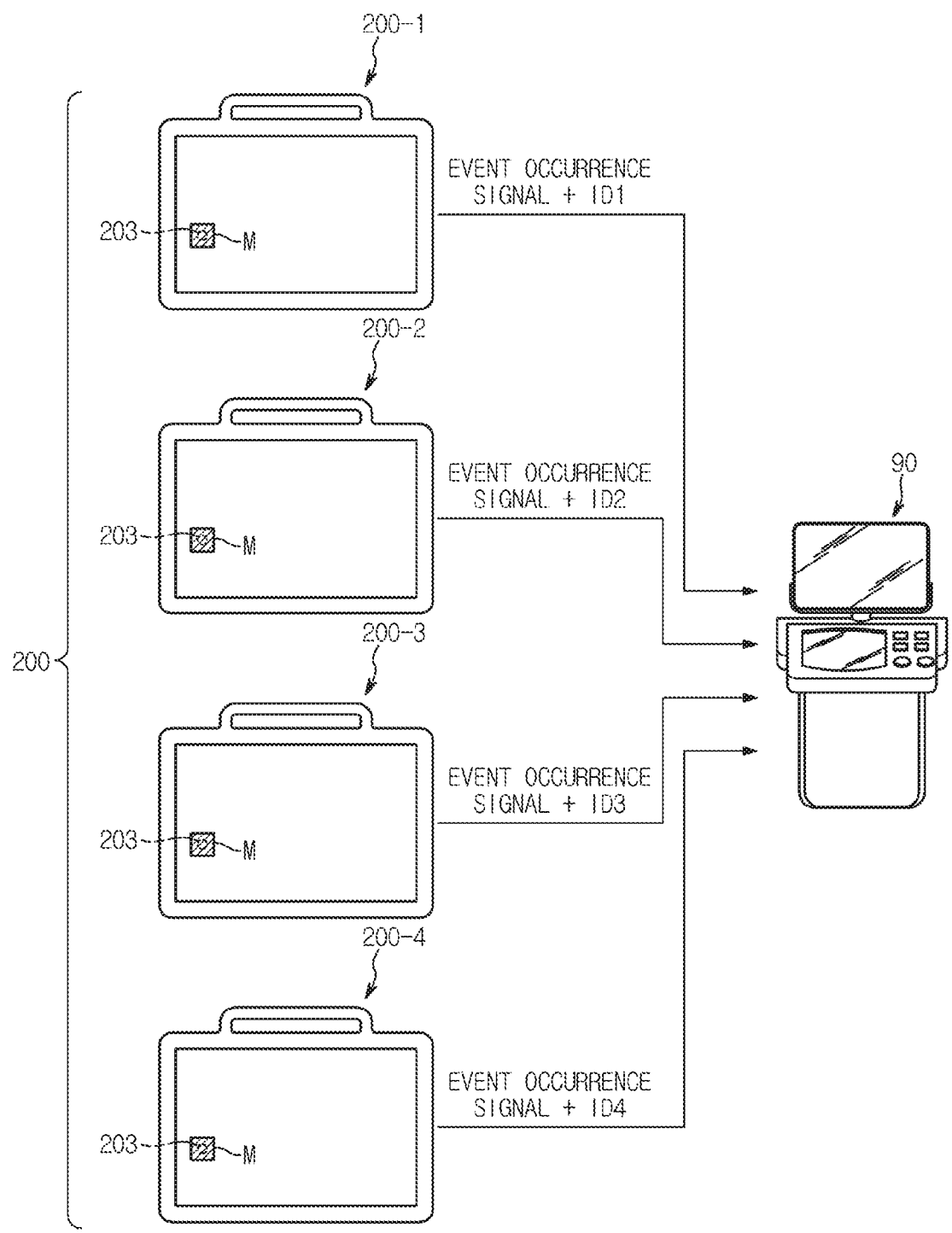
FIG. 13 is a conceptual diagram illustrating examples of signals transmitted to a workstation according to an embodiment.

FIG. 13 is a conceptual diagram illustrating examples of signals transmitted to a single workstation when X-ray detectors are connected to the single workstation according to an embodiment.

In FIG. 13, it is assumed that only one workstation 90 is installed in one imaging room, and four X-ray detectors 200 are connected to the workstation 90. Each of the X-ray detectors 200 may include a magnetic sensor 311 or another type of sensor as described above, e.g., a touch sensor. The X-ray detector 100 may be one of the X-ray detectors 200.

For example, if the predefined event occurs while each of the X-ray detectors 200 connected to the workstation 90 periodically transmits its own status information to the workstation 90, the event occurrence signal may also be transmitted to the workstation 90.

In more detail, if the user moves the magnet M toward the position corresponding to the magnetic sensor of a first X-ray detector 200-1, the controller 130 of the first X-ray detector 200-1 may control the communication interface 140, such that the event occurrence signal and ID information (ID 1) of the first X-ray detector 200-1 may be transmitted to the workstation 90.

The workstation 90 may recognize that the first X-ray detector 200-1 among the X-ray detectors 200 is to be used for the imaging action of the first X-ray detector 200-1, and may perform various configuration actions through which the first X-ray detector 200-1 can be used for X-ray imaging of the object. For example, the configuration action may be carried out based on the size, resolution, etc. of the first X-ray detector 200-1, and it may be possible to configure (or establish) the imaging mode according to whether the first X-ray detector 200-1 is in the stand mode, the table mode, or the portable mode or it may also be possible to adjust the position of the X-ray source 80 according to whether the first X-ray detector 200-1 is in the stand mode, the table mode, or the portable mode.

If the user moves the magnet M toward the position corresponding to the magnetic sensor of a second X-ray detector 200-2, the controller 130 of the second X-ray detector 200-2 may control the communication interface 140 such that the event occurrence signal and ID information (ID 2) of the second X-ray detector 200-2 can be transmitted to the workstation 90.

The workstation 90 may recognize that the second X-ray detector 200-2 among the X-ray detectors 200 is to be used for the imaging action of the second X-ray detector 200-2, and may perform various configuration actions through which the second X-ray detector 200-2 can be used for X-ray imaging of the object.

If the user moves the magnet M toward the position corresponding to the magnetic sensor of a third X-ray detector 200-3, the controller 130 of the third X-ray detector 200-3 may control the communication interface 140 such that the event occurrence signal and ID information (ID 3) of the third X-ray detector 200-3 can be transmitted to the workstation 90.

The workstation 90 may recognize that the third X-ray detector 200-3 among the X-ray detectors 200 is to be used for the imaging action of the third X-ray detector 200-3, and may perform various configuration actions through which the third X-ray detector 200-3 can be used for X-ray imaging of the object.

If the user moves the magnet M toward the position corresponding to the magnetic sensor of a fourth X-ray detector 200-4, the controller 130 of the fourth X-ray detector 200-4 may control the communication interface 140 such that the event occurrence signal and ID information (ID 4) of the fourth X-ray detector 200-4 can be transmitted to the workstation 90.

The workstation 90 may recognize that the fourth X-ray detector 200-4 among the X-ray detectors 200 is to be used for the imaging action of the fourth X-ray detector 200-4, and may perform various configuration actions through which the fourth X-ray detector 200-4 can be used for X-ray imaging of the object.

In addition, as shown in the above-described embodiments, the controller 130 may also configure or establish the drive mode or the imaging mode of the X-ray detector 100 (which may be one of the detectors 200) according to the events detected by the sensor module 110.

The storage 120 may match the drive mode or the imaging mode to the respective predefined events, and may store the matched information therein. If the sensor module 110 detects any of the predefined events, and if the user of the X-ray detector 100 moves the magnet toward the position corresponding to the first sensor 211 according to the drive mode corresponding to the detected event, the controller 130 may determine that the first sensor 211 has detected the predefined event, may search for information associated with the detected event in the storage 120, and may acquire the imaging mode information (indicating the stand mode) corresponding to the first sensor 211 from the storage 120. When the communication interface 140 transmits the event occurrence signal and the ID information of the X-ray detector 100 to the workstation 90, the communication interface 140 may also transmit imaging mode information to the workstation 90. The controller 130 may drive the X-ray detector 100 or may transmit information about the imaging mode corresponding to the driven X-ray detector 100 to the workstation 90.

Figure 14:
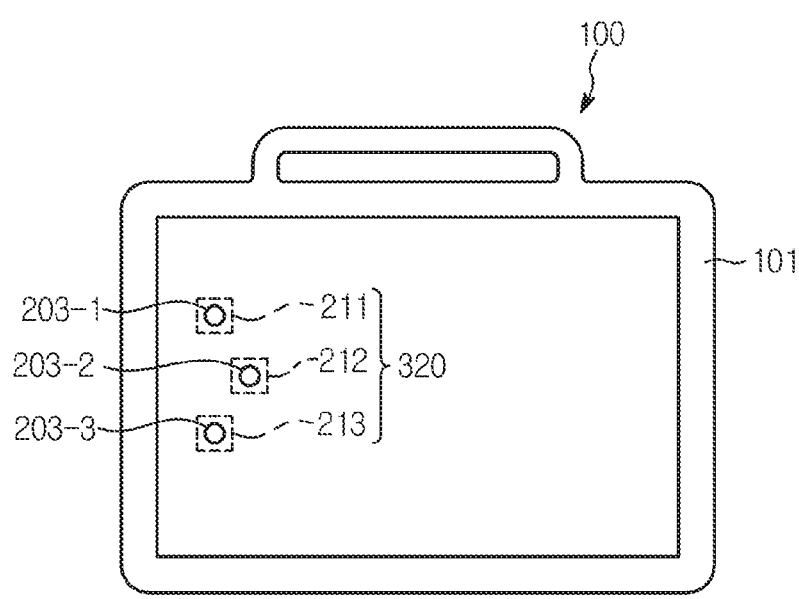
FIG. 14 is a conceptual diagram illustrating examples of a plurality of sensors mounted to an X-ray detector according to an embodiment.

FIG. 14 is a conceptual diagram illustrating examples of a plurality of sensors mounted to an X-ray detector according to an embodiment.

Referring to FIG. 14, the X-ray detector 100 may include sensors 320. The sensors 320 may be, at least partially, the same sensors as the first to fourth sensors 111 to 114 and may be differently configured, or may be, at least in part, physically different sensors. Various configuration of sensors is described above. A plurality of markers 203-1, 203-2, and 203-3 may be formed and displayed at the positions of the housing 101 indicating the respective sensors 320.

For example, a first sensor 211 may be allocated to the stand mode, a second sensor 212 may be allocated to the table mode, and a third sensor 213 may be allocated to the portable mode. Such allocation information may be stored in the storage 120.

If the user moves the magnet toward the position corresponding to the first sensor 211, the controller 130 may determine that the first sensor 211 has detected the predefined event, may search for information associated with the detected event in the storage 120, and may acquire the imaging mode information (indicating the stand mode) corresponding to the first sensor 211 from the storage 120. When the communication interface 140 transmits the event occurrence signal and the ID information of the X-ray detector 100 to the workstation 90, the communication interface 140 may also transmit imaging mode information (indicating the stand mode) to the workstation 90.

If the user moves the magnet toward the position corresponding to the second sensor 212, the controller 130 may determine that the second sensor 212 has detected the predefined event, may search for information associated with the detected event in the storage 120, and may acquire imaging mode information (indicating the table mode) corresponding to the second sensor 212 from the storage 120. When the communication interface 140 transmits the event occurrence signal and the ID information of the X-ray detector 100 to the workstation 90, the communication interface 140 may also transmit imaging mode information (indicating the table mode) to the workstation 90.

If the user moves the magnet toward the position corresponding to the third sensor 213, the controller 130 may determine that the third sensor 213 has detected the predefined event, may search for information associated with the detected event in the storage 120, and may acquire imaging mode information (indicating the portable mode) corresponding to the third sensor 213 from the storage 120. When the communication interface 140 transmits the event occurrence signal and the ID information of the X-ray detector 100 to the workstation 90, the communication interface 140 may also transmit imaging mode information (indicating the portable mode) to the workstation 90.

As described above, the X-ray detector in which the predefined event has occurred, among the plurality of X-ray detectors available in only one imaging room or only one workstation transmits its own ID information and the event occurrence information to the workstation, such that the user does not need to manually input information of the X-ray detector to be used for X-ray imaging, and the user can easily and conveniently perform pairing between the workstation and the X-ray detector.

A method for controlling the X-ray detector according to the embodiments is described in detail below, and the operations and concepts described above with references to FIGS. 1 to 15 may equally be applied to the X-ray detector control method.

Figure 15:
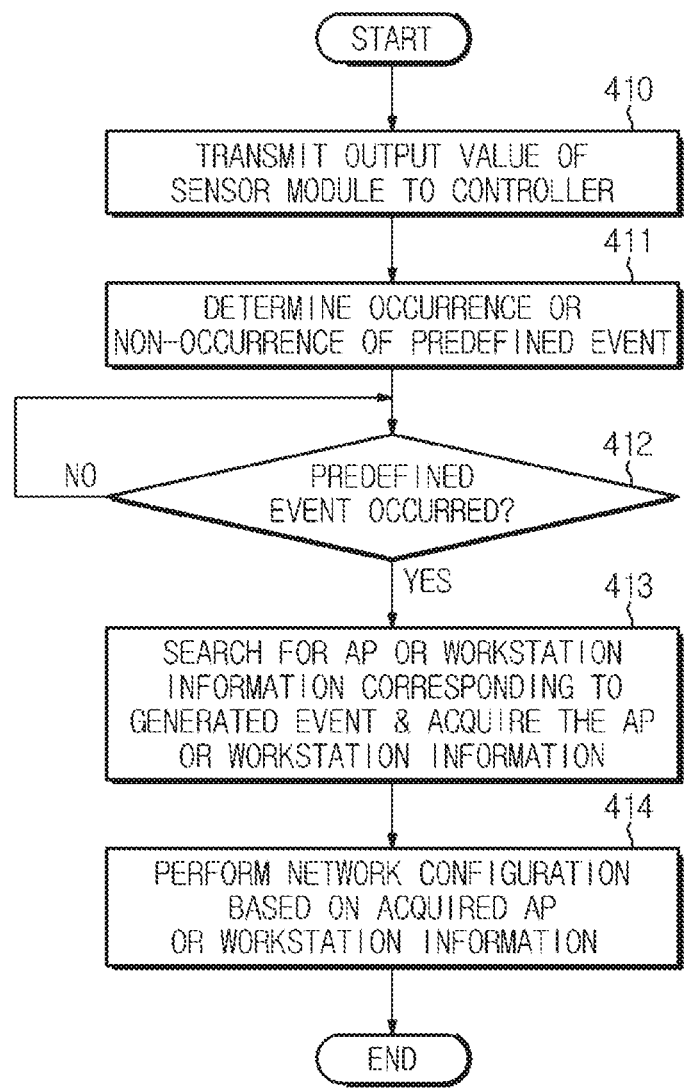
FIG. 15 is a flowchart illustrating a method for controlling an X-ray detector according to an embodiment.

FIG. 15 is a flowchart illustrating a method for controlling the X-ray detector according to an embodiment.

Referring to FIG. 15, the output value of the sensor module 110 may be transmitted to the controller 130 (operation 410). As described above, the sensor module 110 may include at least one of a magnetic sensor, an optical sensor, an IR sensor, an ultrasonic sensor, an acceleration sensor, a touch sensor, a gyro sensor, and/or a temperature sensor.

While the X-ray detector 100 is powered on, the output value of the sensor module 110 may be transmitted to the controller 130 in real time or periodically. If there is a change in output value of the sensor module 110, i.e., only when the event is detected, the X-ray detector 100 may also transmit the output value of the sensor module 110 to the controller 130.

The controller 130 may determine occurrence or non-occurrence of the predefined event based on the output value of the sensor module 110 (operation 411). For this purpose, a reference value to be used as a threshold value for deciding occurrence or non-occurrence of the event may be pre-stored in the storage 120. For example, if the sensor module 110 includes a magnetic sensor and the presence of the approaching magnet M corresponds to the predefined event, an output value corresponding to the magnitude of a magnetic field generated by the magnet M may be pre-stored as a reference value for deciding occurrence or non-occurrence of the event. In addition, provided that the sensor module 110 includes the optical sensor, if approach or contact of the object such as the user finger corresponds to the predefined event, the output value of the sensor module 110 may be pre-stored as a reference value for deciding occurrence or non-occurrence of the event.

If the predefined event has occurred (YES in operation 412), the AP information or workstation information corresponding to the event generated in the storage 120 may be searched for in the storage 120 and may then be acquired from the storage 120 (operation 413). If the sensor module 110 includes a plurality of sensors allocated to the respective APs or the respective workstations, the controller 130 may acquire AP or workstation information corresponding to the sensor in which the event has occurred, from the storage 120. Alternatively, if the sensor module 110 includes a single sensor, and if information segments about the APs or workstations are respectively allocated to the categories or numbers of events generated in the single sensor, it may be possible to acquire AP or workstation information corresponding to the categories or numbers of events detected by the sensor module 110.

The controller 130 may perform network configuration based on the acquired AP or workstation information (operation 414). If network configuration is completed, the communication interface 140 may communicate with the workstation through the access point AP or may be directly coupled to the workstation, such that the communication interface 140 is in a communicable status.

If the predefined event has occurred, the X-detector control method according to an embodiment may further include configuring (or establishing) the imaging mode of the X-ray detector according to the imaging mode information corresponding to the generated event. After completion of the network configuration, the configuring (or establishing) the imaging mode of the X-ray detector may further include transmitting imaging mode information corresponding to the generated event to the workstation 90 connected to the communication interface 140. A detailed description of the process of transmitting the imaging mode information is the same as described above.

If the predefined event has occurred, the X-ray detector control method according to an embodiment may further include configuring (or establishing) a drive mode of the X-ray detector according to drive mode information corresponding to the generated event.

In accordance with above-described embodiments, when only one X-ray detector 100 is used in the plurality of imaging rooms or the plurality of workstations, network configuration can be automatically carried out with the user input generating a simple event whenever a current imaging room or a current workstation is changed to another imaging room or another current workstation, such that the user does not need to manually perform network configuration, resulting in increased user convenience and prevention of erroneous user input actions.

Figure 16:
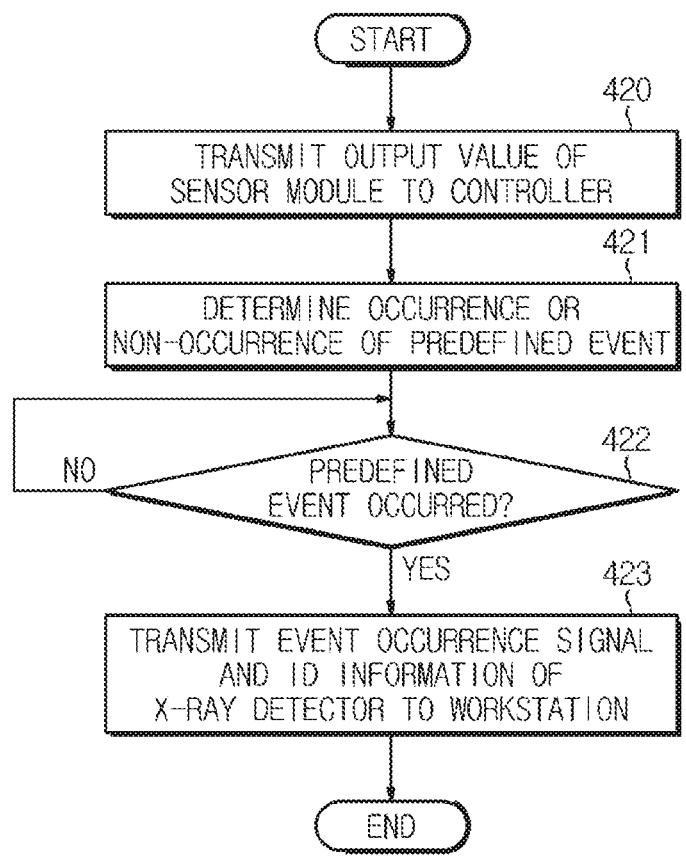
FIG. 16 is a flowchart illustrating a method for controlling an X-ray detector according to an embodiment.

FIG. 16 is a flowchart illustrating a method for controlling an X-ray detector according to an embodiment. The X-ray detector control method according to an embodiment is described below with reference to one of the X-ray detectors 200, for example, the first X-ray detector 200-1.

Referring to FIG. 16, the first X-ray detector 200-1 may transmit an output value of the sensor module 110 to the controller 130 (operation 420). While the first X-ray detector 200-1 is powered on, the output value of the sensor module 110 may be transmitted to the controller 130 in real time or periodically. If there is a change in output value of the sensor module 110, i.e., only when the event is detected, the first X-ray detector 200-1 may also transmit the output value of the sensor module 110 to the controller 130.

The controller 130 may determine whether the predefined event has occurred based on the output value of the sensor module 110 (operation 421). For this purpose, a reference value acting as a threshold value for deciding occurrence or non-occurrence of the event may be pre-stored in the storage 120. A detailed description of the reference value is the same as in FIG. 14.

If the predefined event has occurred (YES in operation 422), the controller 130 may transmit the event occurrence signal and ID information of the first X-ray detector 200-1 to the workstation (operation 423). For example, while each of the X-ray detectors 200 connected to the workstation 90 periodically transmits its own status information to the workstation 90 through the communication interface 140, if the predefined event occurs, each X-ray detector may additionally transmit the event occurrence signal.

Since the predefined event occurs according to the categories of the sensors contained in the sensor module 110 by the user who moves the magnet toward the X-ray detector to be used for X-ray imaging or touches his or her finger on the X-ray detector, the first X-ray detector 200-1 to be used can be automatically paired with the workstation 90.

The X-ray detector control method according to another embodiment may further include transmitting the imaging mode information or configuring (or establishing) the drive mode as described above.

As apparent from the above description, an X-ray detector and a method for controlling the same according to embodiments may allow a sensor module embedded in the X-ray detector to detect a predefined event, and may automatically perform network configuration according to AP information or workstation information corresponding to the detected event, such that a user of the X-ray detector does not need to manually change configuration information of the X-ray detector one by one when the X-ray detector is used in a plurality of imaging rooms or in a plurality of X-ray imaging apparatuses, resulting in greater convenience of the user and prevention of configuration errors by the user.

The X-ray detector allows a sensor module embedded therein to detect a predefined event, and automatically performs network configuration according to AP or workstation information corresponding to the detected event, such that a user of the X-ray detector does not need to manually change configuration information of the X-ray detector even when the X-ray detector is used in several imaging rooms or several X-ray imaging apparatuses, resulting in greater convenience of the user.

Provided that the X-ray detector apparatus is implemented as a plurality of X-ray detectors within one imaging room, i.e., provided that two or more X-ray detectors are used in one imaging room, if any one of the X-ray detectors detects a predefined event using an embedded sensor module therein, the corresponding X-ray detector having detected the predefined event may transmit ID information thereof and a signal indicating occurrence of the event to a workstation, and may be automatically paired with the workstation, such that the user can easily and correctly recognize which one of the plurality of X-ray detectors will be used for X-ray imaging.

Although a few embodiments have been shown and described, it would be appreciated by those skilled in the art that changes may be made in these embodiments without departing from the principles and spirit of aspects of the disclosure, the scope of which is defined in the claims and their equivalents.

What is claimed is:

1. An X-ray detector comprising:
   a sensor module comprising a plurality of sensors configured to sense a plurality of predefined events, respectively;
   a communication interface connectable to a plurality of workstations;
   a memory configured to store a plurality of configuration information in which a configuration information for each of the plurality of workstations, respectively, is stored in correspondence with each of the plurality of sensors; and
   a controller configured to:
      based on an output value of the sensor module, determine an occurrence of a predefined event among the plurality of predefined events, and
      perform a configuration action for the communication interface of the X-ray detector, based on configuration information corresponding to a sensor among the plurality of sensors that detected the predefined event among the stored plurality of configuration information for the plurality of workstations,
   wherein each of the plurality of sensors corresponds to each of the plurality of workstations or each of a plurality of access points (APs) used for connecting the plurality of workstations, respectively, to the communication interface, and
   wherein the controller is further configured to perform the configuration action for the communication interface of the X-ray detector in order to connect a workstation, among the plurality of workstations, which corresponds to the sensor that detected the predefined event.

2. The X-ray detector according to claim 1, wherein the plurality of sensors comprise at least one from among a magnetic sensor, an optical sensor, an infrared (IR) sensor, an ultrasonic sensor, an acceleration sensor, a touch sensor, a gyro sensor, and a temperature sensor, respectively.

3. The X-ray detector according to claim 1, wherein a number of the plurality of sensors is equal to a number of the plurality of workstations or to a number of the plurality of APs.

4. The X-ray detector according to claim 3, wherein the configuration information comprises one from among workstation information and AP information of one of the plurality of APs that is connected to the workstation, and
   the controller is further configured to perform the configuration action for the communication interface based on the one from among the workstation information and the AP information, the one of the workstation information and the AP information corresponding to the sensor having detected the predefined event.

5. The X-ray detector according to claim 1, wherein, based on the occurrence of the predefined event, the controller is further configured to establish connectivity between the communication interface and the workstation based on the configuration information, and transmit imaging mode information corresponding to the predefined event to the workstation connected to the communication interface.

6. The Xray detector according to claim 1, wherein, based on the occurrence of the predefined event, the controller is further configured to set up a drive mode of the X-ray detector according to information about the drive mode corresponding to the predefined event.

7. The X-ray detector according to claim 1, wherein the configuration information comprises one from among a workstation information comprising at least one of an Internet (IP) address of the workstation or a Media Access Control (MAC) address of the workstation and AP information comprising at least one of an IP address of an AP among the plurality of APs that is connected to the workstation or a Service Set Identifier (SSID) of the AP connected to the workstation, and
   the controller is further configured to control the communication interface to establish a connection with the workstation by using the one from among the workstation information and the AP information.

8. The X-ray detector according to claim 1, wherein each of the plurality of sensors comprises one from among a magnetic sensor and a touch sensor.

9. The X-ray detector according to claim 1, further comprising an AP embedded in the X-ray detector and configured to communicate with the plurality of workstations.

10. An X-ray imaging system comprising:
    a first X-ray detector;
    a second X-ray detector; and
    a workstation connectable to one of the first X-ray detector and the second X-ray detector,
    wherein each of the first X-ray detector and the second X-ray detector respectively comprises,
       a sensor module comprising at least one sensor configured to sense a plurality of predefined events;
       a communication interface connectable to the workstation configured to control a plurality of imaging modes comprising at least two modes from among a stand mode, a portable mode, and a table mode;
       a memory configured to store a plurality of imaging mode information in which an imaging mode information for each of the stand mode, the portable mode, and the table mode is stored in correspondence with each of the plurality of predefined events, respectively; and
       a controller configured to:
          based on an output value of the sensor module, determine an occurrence of a predefined event among the plurality of predefined events, and
          transmit an event occurrence signal, identification (ID) information of its own X-ray detector, and an imaging mode information for one imaging mode from among the plurality of imaging mode information stored in the memory, to the workstation.

11. The X-ray imaging system according to claim 10, wherein, based on the occurrence of the predefined event, the controller is further configured to set up a drive mode of the X-ray detector according to drive mode information corresponding to the predefined event, the drive mode comprising at least one from among an auto exposure detection mode and a fast scan mode.

12. The X-ray detector according to claim 10, wherein the at least one sensor is one of a plurality of sensors included in the sensor module, and
a number of the plurality of sensors is equal to a number of the plurality of imaging modes of the X-ray detector.

13. The X-ray detector according to claim 12, wherein the controller is further configured to transmit the imaging mode information corresponding to a sensor having detected the predefined event, among the plurality of sensors.

14. A method for controlling an X-ray detector, the method comprising:
storing, in a memory of the X-ray detector, a plurality of configuration information in which a configuration information for each of a plurality of workstations, respectively, is stored in correspondence with each of a plurality of sensors included in a sensor module of the X-ray detector;
determining an occurrence of a predefined event among a plurality of predefined events, based on an output value of the sensor module; and
performing a configuration action for a communication interface of the X-ray detector, based on configuration information corresponding to a sensor among the plurality of sensors that detected the predefined event among the stored plurality of configuration information for the plurality of workstations,
wherein each of the plurality of sensors corresponds to each of the plurality of workstations or each of a plurality of access points (APs) used for connecting the plurality of workstations, respectively, to the communication interface, and
wherein the performing the configuration action further comprises performing the configuration action for the communication interface of the X-ray detector in order to connect a workstation, among the plurality of workstations, which corresponds to the sensor that detected the predefined event.

15. The method according to claim 14, wherein the plurality of sensors comprise at least one from among a magnetic sensor, an optical sensor, an infrared (IR) sensor, an ultrasonic sensor, an acceleration sensor, a touch sensor, a gyro sensor, and a temperature sensor, respectively.

16. The method according to claim 14, wherein a number of the plurality of sensors included in the sensor module is equal to a number of the plurality of APs or to a number of the plurality of workstations connectable to the communication interface.

17. The method according to claim 16, wherein the configuration information comprises one from among workstation information and AP information of one of the plurality of APs that is connected to the workstation, and the performing the configuration action for the communication interface further comprises:
performing the configuration action for the communication interface based on the one from among the workstation information and the AP information, the one from among the workstation information and the AP information corresponding to the sensor having detected the predefined event.

18. An X-ray detector comprising:
a sensor module comprising a plurality of sensors configured to provide an output value when the sensor module detects an event;
a communication interface connectable a plurality of workstations being disposed in physically separated rooms, respectively;
a memory configured to store configuration information for the communication interface, the configuration information comprising connectivity information of the communication interface to the plurality of workstations, respectively, and a correspondence between each of the plurality of sensors and the connectivity information of each of the plurality of workstations; and
a processor configured to determine an occurrence of a predefined event among a plurality of predefined events, and connect the communication interface to one of the plurality of workstations based on the connectivity information associated with sensor among the plurality of sensors that detected the predefined event,
wherein each of the plurality of sensors corresponds to each of the plurality of workstations or each of a plurality of access points (APs) used for connecting the plurality of workstations, respectively, to the communication interface, and
wherein the processor is further configured to perform a configuration action for the communication interface of the X-ray detector in order to connect a workstation, among the plurality of workstations, which corresponds to the sensor that detected the predefined event.

19. The X-ray detector according to claim 18, wherein the plurality of sensors comprise at least two sensors from among a magnetic sensor, an optical sensor, an infrared (IR) sensor, an ultrasonic sensor, an acceleration sensor, a touch sensor, a gyro sensor, and a temperature sensor, and
the at least two sensors are configured to provide output values indicating the plurality of predefined events.

20. The X-ray detector according to claim 19, wherein the predefined event is generated by a user providing an input through one of the at least two sensors.

21. The X-ray detector according to claim 18, wherein the processor is further configured to connect the communication interface directly to one of the plurality of workstations.

22. The X-ray detector according to claim 18, wherein the processor is further configured to connect the communication interface to one of the plurality of workstations via an AP among the plurality of APs.

* * * * *